United States Patent
Ruth et al.

(10) Patent No.: US 10,413,263 B2
(45) Date of Patent: *Sep. 17, 2019

(54) SYSTEM AND METHOD FOR GENERATING A 2D IMAGE FROM A TOMOSYNTHESIS DATA SET

(71) Applicant: HOLOGIC, INC., Marlborough, MA (US)

(72) Inventors: Christopher Ruth, Boxford, MA (US); Andrew P. Smith, Lexington, MA (US); Jay Stein, Boston, MA (US)

(73) Assignee: HOLOGIC, INC., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/013,782

(22) Filed: Jun. 20, 2018

(65) Prior Publication Data
US 2019/0053776 A1  Feb. 21, 2019

Related U.S. Application Data

(63) Continuation of application No. 15/802,225, filed on Nov. 2, 2017, now Pat. No. 10,010,302, which is a (Continued)

(51) Int. Cl.
*A61B 6/00* (2006.01)
*G06T 11/00* (2006.01)
(Continued)

(52) U.S. Cl.
CPC .............. *A61B 6/502* (2013.01); *A61B 6/025* (2013.01); *A61B 6/461* (2013.01); *A61B 6/463* (2013.01);
(Continued)

(58) Field of Classification Search
CPC ... G06T 7/0024; G06T 11/006; G06T 11/008; G06T 2207/30068; G06T 11/003; A61B 6/502; A61B 6/5229; A61B 6/463
(Continued)

(56) References Cited

U.S. PATENT DOCUMENTS 3,502,878 A   3/1970  Stewart et al.
3,863,073 A   1/1975  Wagner
(Continued)

FOREIGN PATENT DOCUMENTS

DE  102010009295  8/2011
EP      775467      5/1997
(Continued)

OTHER PUBLICATIONS

Mikko Lilja, "Fast and accurate voxel projection technique in free-form cone-beam geometry with application to algebraic reconstruction," Applies Sciences on Biomedical and Communication Technologies, 2008, Isabel '08, first international symposium on, IEEE, Piscataway NJ, Oct. 25, 2008.
(Continued)

*Primary Examiner* — Ali Bayat
(74) *Attorney, Agent, or Firm* — Vista IP Law Group LLP

(57) ABSTRACT

A 2D mammogram image is synthesized from at least one of tomosynthesis projection images and/or the tomosynthesis reconstructed image data. In a simplest form, the mammogram may be synthesized by selecting one of the tomosynthesis projection images for display as a synthesized mammogram. Other methods of synthesizing a mammogram include re-projecting and filtering projection data and/or reconstructed data. The synthesized mammogram is advantageously displayed together with at least a portion of the reconstructed data to aid in review of the reconstructed data.
(Continued)

The present invention thus provides a familiar image which may be used to facilitate review of a tomosynthesis data set.

20 Claims, 12 Drawing Sheets

Related U.S. Application Data continuation of application No. 15/088,844, filed on Apr. 1, 2016, now Pat. No. 9,808,215, which is a continuation of application No. 14/549,604, filed on Nov. 21, 2014, now Pat. No. 9,456,797, which is a continuation of application No. 14/044,959, filed on Oct. 3, 2013, now Pat. No. 8,897,535, which is a continuation of application No. 12/471,981, filed on May 26, 2009, now Pat. No. 8,571,289, which is a continuation-in-part of application No. 12/276,006, filed on Nov. 21, 2008, now Pat. No. 7,760,924.

(51) Int. Cl.
    *A61B 6/02*     (2006.01)
    *G06T 11/60*     (2006.01)
    *G06T 19/20*     (2011.01)
    *G06T 19/00*     (2011.01)

(52) U.S. Cl.
    CPC .......... *G06T 11/003* (2013.01); *G06T 11/006* (2013.01); *G06T 11/008* (2013.01); *G06T 11/60* (2013.01); *G06T 19/00* (2013.01); *G06T 19/20* (2013.01); *G06T 2207/10081* (2013.01); *G06T 2207/10112* (2013.01); *G06T 2207/20221* (2013.01); *G06T 2207/30068* (2013.01); *G06T 2207/30204* (2013.01); *G06T 2210/41* (2013.01); *G06T 2219/2008* (2013.01)

(58) Field of Classification Search
    USPC ....................................................... 382/131
    See application file for complete search history.

(56) References Cited

U.S. PATENT DOCUMENTS

| | | | |
|---|---|---|---|
| 3,971,950 A | 7/1976 | Evans et al. |
| 4,160,906 A | 7/1979 | Daniels |
| 4,310,766 A | 1/1982 | Finkenzeller et al. |
| 4,496,557 A | 1/1985 | Malen et al. |
| 4,559,641 A | 12/1985 | Caugant et al. |
| 4,706,269 A | 11/1987 | Reina et al. |
| 4,744,099 A | 5/1988 | Huettenrauch |
| 4,773,086 A | 9/1988 | Fujita |
| 4,773,087 A | 9/1988 | Plewes |
| 4,819,258 A | 4/1989 | Kleinman et al. |
| 4,821,727 A | 4/1989 | Levene et al. |
| 4,907,156 A | 3/1990 | Doi et al. |
| 4,969,174 A | 11/1990 | Schied |
| 4,989,227 A | 1/1991 | Tirelli et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,133,020 A | 7/1992 | Giger et al. |
| 5,163,075 A | 11/1992 | Lubinsky |
| 5,164,976 A | 11/1992 | Scheid et al. |
| 5,199,056 A | 3/1993 | Darrah |
| 5,240,011 A | 8/1993 | Assa |
| 5,289,520 A | 2/1994 | Pellegrino et al. |
| 5,343,390 A | 8/1994 | Doi et al. |
| 5,359,637 A | 10/1994 | Webbe |
| 5,365,562 A | 11/1994 | Toker |
| 5,415,169 A | 5/1995 | Siczek et al. |
| 5,426,685 A | 6/1995 | Pellegrino et al. |
| 5,452,367 A | 9/1995 | Bick |
| 5,491,627 A | 2/1996 | Zhang et al. |
| 5,506,877 A | 4/1996 | Niklason et al. |
| 5,526,394 A | 6/1996 | Siczek |
| 5,539,797 A | 7/1996 | Heidsieck et al. |
| 5,553,111 A | 9/1996 | Moore |
| 5,592,562 A | 1/1997 | Rooks |
| 5,594,769 A | 1/1997 | Pellegrino |
| 5,596,200 A | 1/1997 | Sharma |
| 5,598,454 A | 1/1997 | Franetzki |
| 5,609,152 A | 3/1997 | Pellegrino et al. |
| 5,627,869 A | 5/1997 | Andrew et al. |
| 5,657,362 A | 8/1997 | Giger et al. |
| 5,668,889 A | 9/1997 | Hara |
| 5,712,890 A | 1/1998 | Spivey et al. |
| 5,719,952 A | 2/1998 | Rooks |
| 5,735,264 A | 4/1998 | Siczek et al. |
| 5,769,086 A | 6/1998 | Ritchart et al. |
| 5,803,912 A | 9/1998 | Siczek et al. |
| 5,818,898 A | 10/1998 | Tsukamoto et al. |
| 5,828,722 A | 10/1998 | Ploetz |
| 5,872,828 A | 2/1999 | Niklason |
| 5,878,104 A | 3/1999 | Ploetz |
| 5,878,746 A | 3/1999 | Lemelson et al. |
| 5,896,437 A | 4/1999 | Ploetz |
| 5,941,832 A | 8/1999 | Tumey |
| 5,986,662 A | 11/1999 | Argiro |
| 6,005,907 A | 12/1999 | Ploetz |
| 6,022,325 A | 2/2000 | Siczek et al. |
| 6,075,879 A | 6/2000 | Roehrig et al. |
| 6,091,841 A | 7/2000 | Rogers |
| 6,137,527 A | 10/2000 | Abdel-Malek |
| 6,141,398 A | 10/2000 | He |
| 6,149,301 A | 11/2000 | Kautzer et al. |
| 6,175,117 B1 | 1/2001 | Komardin |
| 6,196,715 B1 | 3/2001 | Nambu |
| 6,216,540 B1 | 4/2001 | Nelson |
| 6,219,059 B1 | 4/2001 | Argiro |
| 6,256,370 B1 | 4/2001 | Yavus |
| 6,233,473 B1 | 5/2001 | Sheperd |
| 6,243,441 B1 | 6/2001 | Zur |
| 6,272,207 B1 | 8/2001 | Tang |
| 6,289,235 B1 | 9/2001 | Webber et al. |
| 6,292,530 B1 | 9/2001 | Yavus |
| 6,327,336 B1 | 12/2001 | Gingold et al. |
| 6,341,156 B1 | 1/2002 | Baetz |
| 6,375,352 B1 | 4/2002 | Hewes |
| 6,389,104 B1 | 5/2002 | Bani-Hashemi et al. |
| 6,411,836 B1 | 6/2002 | Patel |
| 6,415,015 B2 | 7/2002 | Nicolas |
| 6,442,288 B1 | 8/2002 | Haerer |
| 6,459,925 B1 | 10/2002 | Nields et al. |
| 6,463,181 B2 | 10/2002 | Duarte |
| 6,501,819 B2 | 12/2002 | Unger et al. |
| 6,556,655 B1 | 4/2003 | Chichereau |
| 6,574,304 B1 | 6/2003 | Hsieh |
| 6,597,762 B1 | 7/2003 | Ferrant |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Barnes |
| 6,638,235 B2 | 10/2003 | Miller et al. |
| 6,647,092 B2 | 11/2003 | Eberhard |
| 6,744,848 B2 | 6/2004 | Stanton |
| 6,748,044 B2 | 6/2004 | Sabol et al. |
| 6,751,285 B2 | 6/2004 | Eberhard |
| 6,758,824 B1 | 7/2004 | Miller et al. |
| 6,813,334 B2 | 11/2004 | Koppe |
| 6,882,700 B2 | 4/2005 | Wang |
| 6,885,724 B2 | 4/2005 | Li |
| 6,912,319 B1 | 5/2005 | Barnes |
| 6,940,943 B2 | 9/2005 | Claus |
| 6,978,040 B2 | 12/2005 | Berestov |
| 6,999,554 B2 | 2/2006 | Mertelmeier |
| 7,025,725 B2 | 4/2006 | Dione et al. |
| 7,110,490 B2 | 9/2006 | Eberhard |
| 7,110,502 B2 | 9/2006 | Tsuji |
| 7,123,684 B2 | 10/2006 | Jing et al. |

(56) References Cited

U.S. PATENT DOCUMENTS

| | | |
|---|---|---|
| 7,127,091 B2 | 10/2006 | OpDeBeek |
| 7,142,633 B2 | 11/2006 | Eberhard |
| 7,245,694 B2 | 7/2007 | Jing et al. |
| 7,315,607 B2 | 1/2008 | Ramsauer |
| 7,319,735 B2 | 1/2008 | Defreitas et al. |
| 7,323,692 B2 | 1/2008 | Rowlands |
| 7,346,381 B2 | 3/2008 | Okerlund et al. |
| 7,430,272 B2 | 9/2008 | Jing et al. |
| 7,443,949 B2 | 10/2008 | Defreitas et al. |
| 7,577,282 B2 | 8/2009 | Gkanatsios et al. |
| 7,606,801 B2 | 10/2009 | Faitelson et al. |
| 7,616,801 B2 | 11/2009 | Gkanatsios et al. |
| 7,630,533 B2 | 12/2009 | Ruth et al. |
| 7,702,142 B2 | 4/2010 | Ren et al. |
| 7,760,924 B2 | 7/2010 | Ruth et al. |
| 7,831,296 B2 | 11/2010 | DeFreitas et al. |
| 8,044,972 B2 | 10/2011 | Hall et al. |
| 8,051,386 B2 | 11/2011 | Rosander et al. |
| 8,126,226 B2 | 2/2012 | Bernard et al. |
| 8,155,421 B2 | 4/2012 | Ren et al. |
| 8,165,365 B2 | 4/2012 | Bernard et al. |
| 8,571,289 B2 | 10/2013 | Ruth |
| 8,712,127 B2 | 4/2014 | Ren et al. |
| 8,897,535 B2 * | 11/2014 | Ruth .................... G06T 11/006 |
| | | 382/132 |
| 8,983,156 B2 | 3/2015 | Periaswamy et al. |
| 9,084,579 B2 | 7/2015 | Ren et al. |
| 9,456,797 B2 | 10/2016 | Ruth et al. |
| 9,805,507 B2 | 10/2017 | Chen |
| 9,811,758 B2 | 11/2017 | Ren et al. |
| 2001/0038861 A1 | 11/2001 | Hsu et al. |
| 2002/0012450 A1 | 1/2002 | Tsuji |
| 2002/0050986 A1 | 5/2002 | Inoue |
| 2002/0075997 A1 | 6/2002 | Unger et al. |
| 2003/0007598 A1 | 1/2003 | Wang |
| 2003/0018272 A1 | 1/2003 | Treado et al. |
| 2003/0026386 A1 | 2/2003 | Tang |
| 2003/0073895 A1 | 4/2003 | Nields et al. |
| 2003/0095624 A1 | 5/2003 | Eberhard et al. |
| 2003/0128893 A1 | 7/2003 | Castorina |
| 2003/0169847 A1 | 9/2003 | Karellas |
| 2003/0194050 A1 * | 10/2003 | Eberhard ................ A61B 6/037 |
| | | 378/37 |
| 2003/0194121 A1 | 10/2003 | Eberhard et al. |
| 2003/0210254 A1 | 11/2003 | Doan |
| 2003/0212327 A1 | 11/2003 | Wang |
| 2003/0215120 A1 | 11/2003 | Uppaluri |
| 2004/0008809 A1 | 1/2004 | Webber |
| 2004/0008901 A1 | 1/2004 | Avinash |
| 2004/0047518 A1 | 3/2004 | Tiana |
| 2004/0052328 A1 | 3/2004 | Saboi |
| 2004/0066884 A1 | 4/2004 | Hermann Claus et al. |
| 2004/0066904 A1 | 4/2004 | Eberhard et al. |
| 2004/0070582 A1 | 4/2004 | Smith et al. |
| 2004/0094167 A1 | 5/2004 | Brady |
| 2004/0101095 A1 | 5/2004 | Jing et al. |
| 2004/0109529 A1 | 6/2004 | Eberhard et al. |
| 2004/0171986 A1 | 9/2004 | Tremaglio, Jr. et al. |
| 2004/0267157 A1 | 12/2004 | Miller et al. |
| 2005/0049521 A1 | 3/2005 | Miller et al. |
| 2005/0063509 A1 | 3/2005 | Defreitas et al. |
| 2005/0078797 A1 | 4/2005 | Danielsson et al. |
| 2005/0105679 A1 | 5/2005 | Wu et al. |
| 2005/0113681 A1 | 5/2005 | DeFreitas |
| 2005/0113715 A1 | 5/2005 | Schwindt et al. |
| 2005/0135555 A1 | 6/2005 | Claus |
| 2005/0135664 A1 | 6/2005 | Kaufhold |
| 2005/0226375 A1 | 10/2005 | Eberhard |
| 2006/0018526 A1 | 1/2006 | Avinash |
| 2006/0030784 A1 | 2/2006 | Miller et al. |
| 2006/0074288 A1 | 4/2006 | Kelly et al. |
| 2006/0098855 A1 | 5/2006 | Gkanatsios |
| 2006/0129062 A1 | 6/2006 | Nicoson et al. |
| 2006/0155209 A1 | 7/2006 | Miller et al. |
| 2006/0291618 A1 | 12/2006 | Eberhard et al. |
| 2007/0030949 A1 | 2/2007 | Jing et al. |
| 2007/0036265 A1 | 2/2007 | Jing et al. |
| 2007/0052700 A1 | 3/2007 | Wheeler et al. |
| 2007/0076844 A1 | 4/2007 | Defreitas et al. |
| 2007/0223651 A1 | 9/2007 | Wagenaar et al. |
| 2007/0225600 A1 | 9/2007 | Weibrecht et al. |
| 2007/0242800 A1 | 10/2007 | Jing et al. |
| 2008/0045833 A1 | 2/2008 | Defreitas et al. |
| 2008/0130979 A1 | 6/2008 | Ren |
| 2008/0187095 A1 | 8/2008 | Boone et al. |
| 2009/0003519 A1 | 1/2009 | Defreitas et al. |
| 2009/0005668 A1 | 1/2009 | West et al. |
| 2009/0010384 A1 | 1/2009 | Jing et al. |
| 2009/0034684 A1 * | 2/2009 | Bernard .................. G06T 19/00 |
| | | 378/98 |
| 2009/0080594 A1 | 3/2009 | Brooks et al. |
| 2009/0080602 A1 | 3/2009 | Brooks et al. |
| 2009/0080765 A1 | 3/2009 | Bernard et al. |
| 2009/0123052 A1 | 5/2009 | Ruth |
| 2009/0135997 A1 | 5/2009 | Defreitas et al. |
| 2009/0238424 A1 | 9/2009 | Arakita |
| 2009/0268865 A1 | 10/2009 | Ren et al. |
| 2009/0296882 A1 | 12/2009 | Gkanatsios et al. |
| 2009/0304147 A1 | 12/2009 | Jing et al. |
| 2010/0054400 A1 | 3/2010 | Ren et al. |
| 2010/0086188 A1 | 4/2010 | Ruth et al. |
| 2010/0135558 A1 | 6/2010 | Ruth et al. |
| 2010/0195882 A1 | 8/2010 | Ren et al. |
| 2010/0259645 A1 | 10/2010 | Kaplan |
| 2011/0069906 A1 | 3/2011 | Park |
| 2011/0109650 A1 | 5/2011 | Kreeger et al. |
| 2011/0110576 A1 | 5/2011 | Kreeger et al. |
| 2011/0178389 A1 | 7/2011 | Kumar et al. |
| 2011/0234630 A1 | 9/2011 | Batman et al. |
| 2011/0242092 A1 | 10/2011 | Kashiwagi |
| 2012/0293511 A1 | 11/2012 | Mertelmeier |
| 2014/0327702 A1 | 11/2014 | Kreeger et al. |
| 2015/0317538 A1 | 11/2015 | Ren et al. |
| 2018/0047211 A1 | 2/2018 | Chen et al. |
| 2018/0137385 A1 | 5/2018 | Ren |
| 2019/0043456 A1 | 2/2019 | Kreeger et al. |

FOREIGN PATENT DOCUMENTS

| | | |
|---|---|---|
| EP | 982001 | 3/2000 |
| EP | 1428473 | 6/2004 |
| EP | 2215600 | 8/2010 |
| EP | 2301432 | 3/2011 |
| JP | 2003-189179 | 7/2003 |
| JP | 2007-536968 | 12/2007 |
| JP | 2009-207545 | 9/2009 |
| WO | WO 90/05485 | 5/1990 |
| WO | WO 9816903 | 4/1998 |
| WO | WO 00/51484 | 9/2000 |
| WO | WO 03020114 | 3/2003 |
| WO | WO 2005051197 | 6/2005 |
| WO | WO 2005110230 | 11/2005 |
| WO | WO 2005112767 | 12/2005 |
| WO | WO 2006055830 | 5/2006 |
| WO | WO 2006058160 | 6/2006 |
| WO | WO 2008047270 | 4/2008 |
| WO | WO 2010059920 | 5/2010 |
| WO | WO 2011008239 | 1/2011 |
| WO | WO 2011065950 | 6/2011 |
| WO | WO 2011073864 | 6/2011 |
| WO | WO 2011091300 | 7/2011 |
| WO | WO 2012063653 | 5/2012 |

OTHER PUBLICATIONS

Pediconi, "Color-coded automated signal intensity-curve for detection and characterization of breast lesions: Preliminary evaluation of new software for MR-based breast imaging," International Congress Series 1281 (2005) 1081-1086.

Heang-Ping, Roc "Study of the effect of stereoscopic imaging on assessment of breast lesions," Medical Physics, vol. 32, No. 4, Apr. 2005.

(56) References Cited

OTHER PUBLICATIONS

Amendment Response to Final Office Action for U.S. Appl. No. 12/276,006 dated Mar. 24, 2010 (6 pages).
Amendment Response to Non-Final Office Action for U.S. Appl. No. 12/276,006 dated Sep. 28, 2009 (8 pages).
Final Office Action dated Jan. 20, 2010 for U.S. Appl. No. 12/276,006.
Non-Final Office Action dated Jun. 25, 2009 for U.S. Appl. No. 12/276,006.
Amendment Resonse after Final Office Action for U.S. Appl. No. 12/471,981 dated Apr. 3, 2013 (6 pages).
Amendment Response to Non-Final Office Action for U.S. Appl. No. 12/471,981 dated Dec. 10, 2012 (6 pages).
Non-Final Office Action dated Feb. 13, 2013 for U.S. Appl. No. 12/471,981.
Non-Final Office Action dated Aug. 10, 2012 for U.S. Appl. No. 12/471,981.
Amendment Response to Non-Final Office Action for U.S. Appl. No. 14/044,959 dated May 13, 2014 (8 pages).
Non-Final Office Action dated Feb. 13, 2014 for U.S. Appl. No. 14/044,959.
Foreign Office Action for CN Application No. 200980101409.X dated Jun. 26, 2014.
Foreign Office Action for EP Patent Application No. 09796173.4 dated Apr. 11, 2014.
Foreign Office Action for JP Patent Application No. 2011-537644 dated Jul. 29, 2013.
Foreign Office Action for JP Patent Application No. 2014-047021 dated Jan. 21, 2015.
International Search Report for International Publication No. PCT/US2009/065288 dated Jan. 29, 2014.
International Preliminary Report on Patentability for International Publication No. PCT/US2012/066526 dated May 27, 2014.
PCT Notification of International Search Report and Written Opinion for PCT/US2012/066526, Applicant Hologic, Inc., dated Feb. 6, 2013 (7 pages).
International Preliminary Report on Patentability for International Publication No. PCT/US2013/025993 dated Aug. 19, 2014.
International Search Report and Written Opinion for International Publication No. PCT/US2013/025993 dated Apr. 26, 2013.
Foreign office action from JP 2014-543604 dated Oct. 4, 2016.
Extended EP Search Report for EP Application No. 13749870.5 dated Oct. 7, 2015, 7 pages.
Extended EP Search Report for EP Application No. 12851085.6, dated Jan. 6, 2015, 6 pages.
Giger et al. "Development of a smart workstation for use in mammography", in Proceedings of SPIE, vol. 1445 (1991), pp. 101 103; 4 pages.
Giger et al., "An Intelligent Workstation for Computer-aided Diagnosis", in RadioGraphics, May 1993, 13:3 pp. 647 656; 10 pages.
Non final office action dated Jan. 22, 2016 for U.S. Appl. No. 14/360,389.
"Predicting tumour location by simulating large deformations of the breast using a 3D finite element model and nonlinear elasticity" by P. Pathmanathan et al., Medical Image Computing and Computer-Assisted Intervention, pp. 217-224, vol. 3217 (2004).
"ImageParser: a tool for finite element generation from three-dimensional medical images" by H. M. Yin et al., BioMedical Engineering OnLine. 3:31, pp. 1-9, Oct. 1, 2004.
"Biomechanical 3-D Finite Element Modeling of the Human Breast Using MRI Data" by A. Samani et al. IEEE Transactions on Medical Imaing, vol. 20, No. 4, pp. 271-279. 2001.
"Mammogram synthesis using a 3D simulation. I. breast tissue model and image acquisition simulation" by Bakic et al., Medical Physics. 29, pp. 2131-2139 (2002).

Non Final Office action dated Nov. 20, 2015 for U.S. Appl. No. 14/549,604.
Response to Non Final Office action submitted May 23, 2016 for U.S. Appl. No. 14/360,389.
Final Office Action dated Jul. 5, 2016 for U.S. Appl. No. 14/360,389.
Response to Final Office Action submitted Aug. 15, 2016 for U.S. Appl. No. 14/360,389.
Advisory Action dated Aug. 24, 2016 for U.S. Appl. No. 14/360,389.
Pre-Appeal Brief Request for Review submitted Oct. 4, 2016 for U.S. Appl. No. 14/360,389.
Appeal Brief submitted Dec. 4, 2016 for U.S. Appl. No. 14/360,389.
Examiner's Answer to Appeal Brief dated Jan. 31, 2017 for U.S. Appl. No. 14/360,389.
Reply Brief submitted Mar. 6, 2017 for U.S. Appl. No. 14/360,389.
Decision on Appeal dated Nov. 8, 2017 for U.S. Appl. No. 14/360,389.
Non-Final Office Action dated Mar. 9, 2017 for U.S. Appl. No. 15/088,844.
Notice of Allowance for U.S. Appl. No. 15/088,844 dated Jun. 29, 2017.
Notice of Allowance for U.S. Appl. No. 15/088,844 dated Mar. 28, 2017.
Office Action dated Mar. 10, 2017 for Canadian Application No. 2,702,782, Owner Hologic, Inc., based on PCT/US2009/065288, 3 pages.
Office Action dated Jan. 11, 2017 for Japanese Patent Application No. 2014-556824, Applicant Hologic, Inc., including English Translation provided by Japanese associate, 12 pages.
Computer generated translation of Foreign Patent Reference JP 2003-189179 A, published Jul. 4, 2003,16 pages.
International Preliminary Report on Patentability for International Publication No. PCT/US2009/065288 dated Feb. 18, 2014.
Notice of Allowance dated Jan. 22, 2018 for U.S. Appl. No. 14/360,389.
Office action dated Feb. 1, 2018 for U.S. Appl. No. 15/802,225.
Office Action dated Feb. 19, 2018 for EP Application 12851085.6, Applicant Hologic, Inc. 5 pp.
Extended EP Search Report for EP Application No. 17176956.5 dated Apr. 3, 2018, 7 pages.
Notice of Allowance dated May 21, 2018 for U.S. Appl. No. 14/360,389.
Office action dated Aug. 27, 2018 for U.S. Appl. No. 15/794,635.
Amendment response to office action filed Nov. 14, 2018 for U.S. Appl. No. 15/794,635.
Notice of Allowance dated Jan. 17, 2019 for U.S. Appl. No. 15/794,635.
European search report in connection with corresponding European patent application No. EP 06255790, dated Aug. 17, 2007.
European search report in connection with counterpart European Patent Application No. 05824734, dated May 9, 2011.
PCT International Search Report and Written Opinion dated Sep. 25, 2008, for International Application No. PCT/US2005/041941, Applicant Hologic, Inc., 8 pages.
Non Final Office Action dated Sep. 21, 2016 for U.S. Appl. No. 14/744,930.
Response to Non Final Office action filed Dec. 14, 2016 for U.S. Appl. No. 14/744,930.
Final Office Action dated Mar. 31, 2017 for U.S. Appl. No. 14/744,930.
Response to Final Office action filed Aug. 2, 2017 for U.S. Appl. No. 14/744,930.
Non Final Office action dated May 18, 2018 for U.S. Appl. No. 15/804,915.
Response to Non Final Office Action filed Aug. 20, 2018 for U.S. Appl. No. 15/804,915.

\* cited by examiner

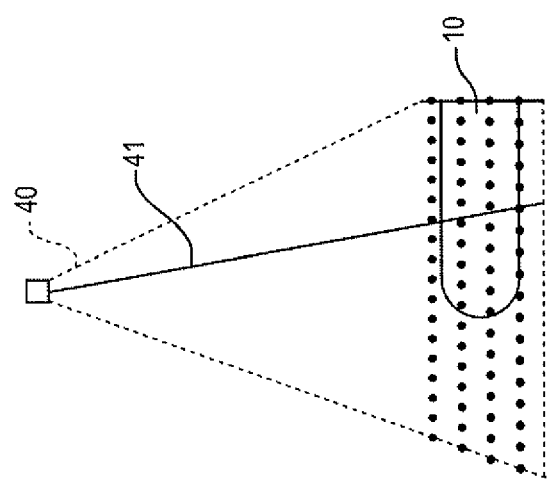
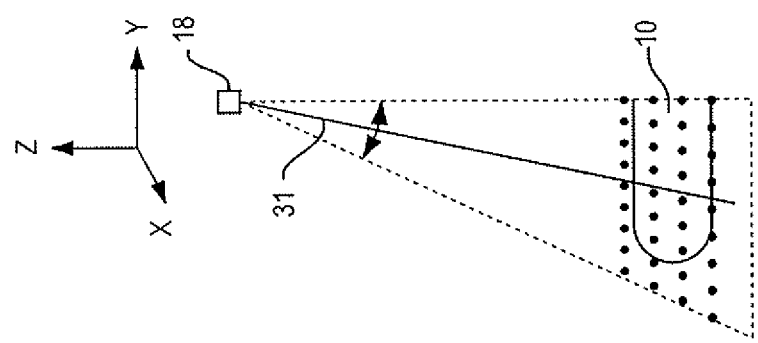
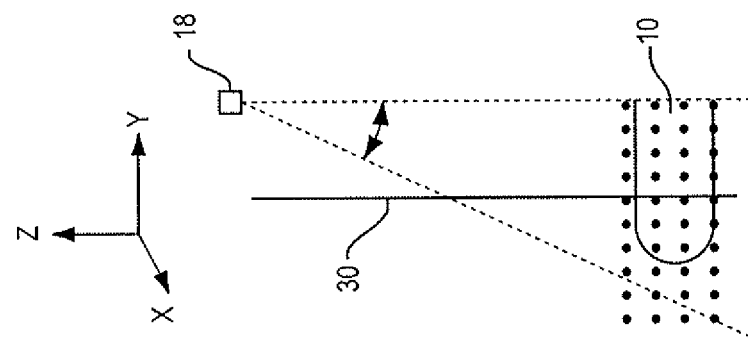

SYSTEM AND METHOD FOR GENERATING A 2D IMAGE FROM A TOMOSYNTHESIS DATA SET

RELATED APPLICATIONS

This application is a continuation application of, and claims priority under 35 U.S.C. § 120 to, U.S. patent application Ser. No. 15/802,225, filed Nov. 2, 2017, now U.S. Pat. No. 10,010,302, which is a continuation of U.S. Pat. No. 9,808,215, filed Apr. 1, 2016, which is a continuation of U.S. Pat. No. 9,456,797, filed Nov. 21, 2014, which is a continuation of U.S. Pat. No. 8,897,535, filed Oct. 3, 2013, which is a continuation of U.S. Pat. No. 8,571,289, filed May 26, 2009, which is a continuation in part of U.S. Pat. No. 7,760,924, filed Nov. 21, 2008. Each of the above applications is hereby incorporated by reference in its entirety, as though set forth in full.

FIELD

This patent specification pertains to x-ray mammography and tomosynthesis, and more specifically to techniques and equipment for acquiring and/or synthesizing, processing, storing and displaying mammograms, tomosynthesis projection images, synthesized two-dimensional (2D) images and tomosynthesis reconstructed images, and to medical image softcopy reading systems, to hanging protocols and to other medical image display features.

BACKGROUND

Mammography has long been used to screen for breast cancer and other abnormalities and for diagnostics. Traditionally, mammograms were formed on X-ray film, but more recently flat panel digital imagers have been introduced that acquire a mammogram in digital form and thereby facilitate analysis and storage and provide other benefits as well. Further, X-ray tomosynthesis of the breast has been proposed recently, as discussed in the earlier-filed applications identified above, and clinical testing has been carried out. The assignee of this patent specification, Hologic, Inc., has demonstrated at trade shows in this country a fused, multi-mode mammography/tomosynthesis system that takes either or both types of images, either while the breast remains immobilized or in different compressions of the breast.

Dedicated breast tomosynthesis systems also have been proposed. However, in clinical use it can be desirable for a number of reasons to assess both tomosynthesis images and conventional mammograms of the patient's breast. For example, the decades of conventional mammograms have enabled medical professionals to develop valuable expertise. Mammograms offer good visualization of micro-calcifications, and can offer higher spatial resolution when compared with tomosynthesis images. While tomosynthesis images provided by dedicated breast tomosynthesis systems in the art have other desirable characteristics (i.e., better visualization of structures), such systems do not leverage the existing interpretation expertise of medical professionals. In addition, the increased mobility of patient data and varied capabilities of imaging centers will require the ability to provide mechanisms that enable images to be displayed using whatever resources are available at the imaging center, without regard to the original acquisition format of the image.

SUMMARY

Tomosynthesis as used in the systems and methods disclosed in this patent specification typically involves acquiring a plurality of tomosynthesis projection images Tp at respective angles relative to the breast, and reconstructing there from a plurality of tomosynthesis reconstructed images Tr representative of breast slices that have selective thicknesses. According to one aspect of the invention, a synthesized 2D image is generated using at least one of the tomosynthesis projection images TP and/or the tomosynthesis reconstructed images Tr. The reconstructed images may be reconstructed using any one of a variety of techniques, including but not limited to filtered back projection in either spatial or frequency domain, maximum likelihood reconstruction, iterative reconstruction, reconstruction using algebraic methods, minimum likelihood or other known or developed three dimensional reconstruction methods. The may be obtained using projection data obtained based on any coordinate system, including a Cartesian coordinate system, a cone beam coordinate system, where the cone beam coordinate system may be defined by geometric information of an associated tomosynthesis acquisition system or alternatively may be a virtualized cone beam coordinate system defined relative to a 'virtual' tomosynthesis acquisition system. Further, following reconstruction, the reconstructed data may projected onto any other different coordinate system; for example, reconstruction data obtained using a first coordinate system may be projected into a second, different coordinate system. For example onto reconstructed data may be projected onto a plane of a different orientation, a cone beam reconstruction may be projected onto a virtual cone beam coordinate system or a Cartesian coordinate system, etc. In summary, projection images may be reconstructed onto any first coordinate system and then projected onto any second, different coordinate system.

The synthesized 2 D image is referred to herein as a synthesized mammogram (Ms) or other synthesized 2D tomosynthesis image (T2d). The synthesized 2D image may be generated using any combination of tomosynthesis projection data or reconstructed data generated using from, or projected onto, any coordinate system. The synthesized 2D image of the present invention is advantageously displayed together with tomosynthesis image data (Tr and/or Tp images) at a review workstation. With such an arrangement, a medical professional may utilize existing expertise gained from past review of mammogram data to more efficiently assess and view the 3D tomosynthesis data, without independent acquisition of a mammogram.

In another embodiment, the synthesized 2D image Ms may be displayed together with an Mp image previously obtained for the patient, to enable comparison of like images using known methods before using the Tr data. Conversely, the method of synthesizing 2D images from Tp and/or Tr data may be used to compare mammograms obtained by a mammography-only machine against existing tomosynthesis data for a patient, thereby increasing the utility of tomosynthesis data by facilitating transport between systems of differing capabilities. Thus there are a variety of systems, including mammo only systems, tomo only systems and combo systems, which may benefit from the ability to synthesize a 2D image from tomosynthesis data, either for comparison with mammography data, or increasing the efficiency of diagnostic workflow.

Proper display techniques make the presentation of Ms, Mp, Tp and/or Tr images (collectively referred to here as T images) more effective and efficient for review by health professionals. When tomosynthesis projection images Tp are acquired, (with or without conventional 2D mammograms Mp) improved display methods facilitate the display of both T and Mp and/or Ms images.

Effective display approaches also are desirable when tomosynthesis images Tp and/or Tr that are acquired at one time need to be compared to mammograms Mp and/or to tomosynthesis images Tp and/or Tr acquired at a different time. In situations where an Mp image is not available for a particular time, but Tp and/or Tr images are available, the present invention enables generation of a synthesized mammogram image Ms. Effective displays also are desirable when only Tr and/or Tp images are being displayed.

An Ms image may be provided in any number of ways using one or more Tp images and/or one or more Tr images. A variety of techniques for generating Ms images will be described in more detail below. The Ms image may be dynamically generated prior to display, or alternatively may be pre-generated and stored. For example, Ms images may be dynamically synthesized prior to display of Tr/Tp images, may be generated upon acquisition of the Tp images and stored with Tp images, or may be generated following reconstruction of the Tr images, using a combination of Tp and Tr images.

The display may be adapted to provide concurrent, toggled, overlaid or cine display of any combination of one or more of the Ms, Mp, Tp and Tr images. Concurrent display may be in the form of a side by side view, either on the same display or on neighboring displays, or alternatively may be in the form of a thumbnail scout view of one image provided within another image. When viewing images concurrently, the present invention supports reflective marking of the different images; for example should the technician mark an area of interest on the mammogram (or tomo slice) or move a marker on the mammogram, the mark and/or movement of the mark is reflected in the appropriate location of the tomo slice (or mammogram).

Another display issue relates to Computer Aided Detection (CAD) methods that use computer analysis of images to identify locations and possibly other characteristics of suspected abnormalities. CAD marks currently are placed on or are otherwise associated with mammogram images Mp, but it may be useful to place them at the appropriate location on Tr and/or Tp images or to otherwise associate them with Tr/Tp images. Conversely, it may be desirable to obtain CAD marks by processing Tp and/or Tr images, and place them at appropriate locations on Mp images, or alternatively at appropriate locations in an Ms image.

BRIEF DESCRIPTION OF DRAWINGS

FIG. 3 illustrates an example where four units acquiring Tp images feed a single unit that reconstructs Tr images.

FIGS. 11a-11c illustrate, respectively, tomosynthesis reconstruction into a Cartesian geometry, into a cone-beam geometry and into a virtual geometry.

DETAILED DESCRIPTION OF PREFERRED EMBODIMENTS

Figure 1:
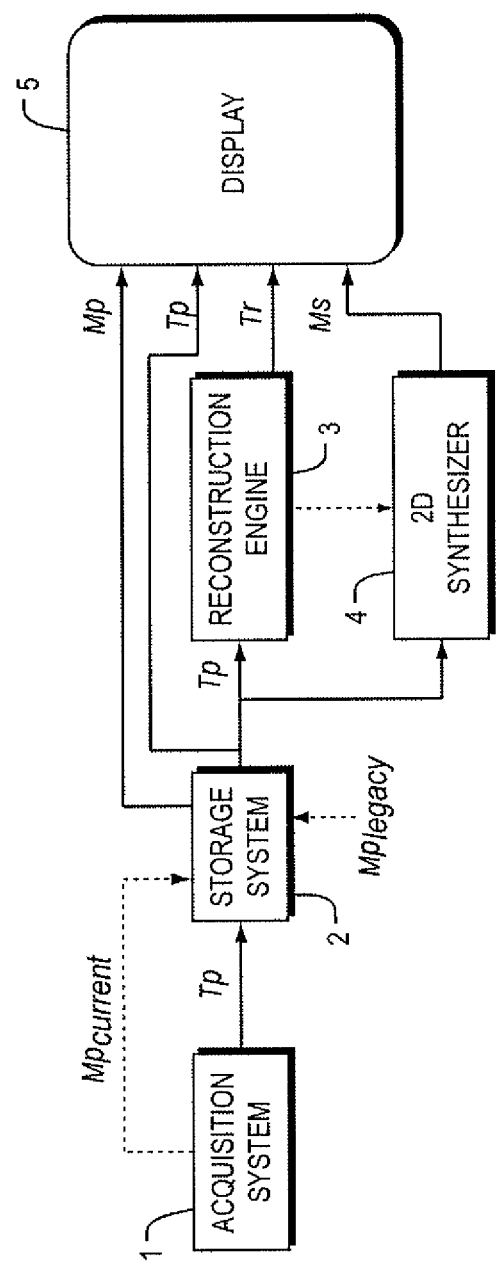
FIG. 1 is a block diagram illustrating flow of data through a system which includes a combination mammography/tomosynthesis acquisition station or a tomosynthesis only acquisition station and where reconstruction of tomosynthesis slice images Tr and synthesis of the Ms images occurs after storage of acquired tomosynthesis projection images Tp.

In describing preferred embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

The following abbreviations shall have the following definitions throughout this application. The notation Mp refers to a conventional mammogram, which is a two-dimensional projection image of a breast and encompasses both a digital image as acquired by a flat panel detector or another imaging device and the image after conventional processing to prepare it for display to a health professional or for storage, e.g. in the PACS system of a hospital or another institution. The term $Mp_{current}$ refers to a mammogram that is acquired by an acquisition system for patient diagnosis, while the term $Mp_{legacy}$ refers to a mammogram image of a patient that had been taken on a previous review of the patient, for example one that is to be used for comparison against an $Mp_{current}$ to identify changes in a patient's breast structure.

Tp refers to an image that is similarly two-dimensional but is taken at a respective tomosynthesis angle between the breast and the origin of the imaging X-rays (typically the focal spot of an X-ray tube), and also encompasses the image as acquired as well as the image after being processed for display or for some other use. Tr refers to an image that is reconstructed from images Tp, for example in the manner described in said earlier-filed patent applications, and represents a slice of the breast as it would appear in a projection X-ray image of that slice at any desired angle, not only at an angle used for Tp or Mp images.

The term Ms refers to synthesized 2D projection images which simulate mammography images, such as a craniocaudal (CC) or mediolateral oblique (MLO) images, and are constructed using tomosynthesis projection images Tp, tomosynthesis reconstructed images Tr or a combination thereof. Ms images may be provided for display to a health professional or for storage in the PACS system of a hospital or another institution.

The terms Tp, Tr, Ms and Mp also encompasses information, in whatever form, that is sufficient to describe such an image for display, further processing, or storage. The images Mp, Ms. Tp and Tr typically are in digital form before being displayed, and are defined by information identifying properties of each pixel in a two-dimensional array of pixels. The pixel values typically relate to respective measured or estimated or computed responses to X-rays of corresponding volumes in the breast (voxels or columns of tissue). In a preferred embodiment, the geometry of the tomosynthesis images (Tr and Tp) and mammography images (Ms, Mp) are matched to a common coordinate system as described in U.S. patent application Ser. No. 11/667,650 "Matching Geometry Generation and Display of Mammograms and Tomosynthesis Images", filed Nov. 15, 2005 and incorporated herein by reference.

FIG. 1 illustrates flow of data in one example of an image generation and display system disclosed in this patent specification. An image data acquisition system 1 acquires tomosynthesis image data for Tp images of patients' breasts, and can take the form of and use the acquisition methods of any of the systems disclosed in said earlier-filed patent applications. If the system is a combo system, Mp images may also be generated (as indicated by dashed line and label $Mp_{current}$ in FIG. 1). Some dedicated tomosynthesis systems or combo systems may be adapted to accept and store legacy mammogram images (indicated via dashed line and legend $Mp_{legacy}$ in FIG. 1) in a Picture Archiving and Communication System (PACS) storage device 2, although it is not a requirement that any Mp images be acquired or pre-stored.

Following tomosynthesis image acquisition, the data describing projection images Tp are sent to storage device 2, which is preferably a DICOM-compliant PACS. When images are needed for display 5, the data Tp images are sent, from either acquisition system 1 or from storage device 2, to a computer system 3 configured as a reconstruction engine that can perform tomosynthesis reconstruction into images Tr representing breast slices of selected thickness and at selected orientations, as disclosed in said earlier-filed patent applications and detailed below. The computer system may be further configured with 2D synthesis functionality 4, which may operate substantially in parallel with reconstruction engine 3 to generate a synthesized 2D image (interchangeably referenced as T2d or Ms). The reconstructed slice images Tr are then sent to a display system 5 so that they can be viewed. If the reconstruction engine 3 is connected to display 5 via a fast link, then large datasets can be transmitted quickly. Other images, such as the Ms, Mp and/or Tp images may also be forwarded to the display unit for concurrent or toggled viewing.

Over time, there will likely be improvements to the acquisition systems and to the display systems, which may result in hardware and software upgrades and changes to reconstruction algorithms. This can create issues in viewing images taken previously. It may be important to be able to recall from storage and reconstruct an image that looks identical (or is at least comparable) to the way it looked when it was reconstructed and displayed in the past, or vice versa.

Consider the example where an improvement in reconstruction algorithms improves image quality so as to allow detection of a cancerous lesion in an image where it was not visible using a previous version of the reconstruction algorithm and the then existing standard of care. While it could be useful to see older images processed with the newer algorithms, it may also be important to allow the re-display of images as they were viewed during an original detection/diagnosis. One way to accomplish this in accordance with the disclosure in this patent specification is to put a version number or some other information in the data for Tp images, which identifies the software and/or hardware versions of the Tp image data acquisition and/or Tr image reconstruction system at the time of acquisition, or to otherwise associate such information with the Tp images. During reconstruction at a later time, the reconstruction engine reads this version number or other similar information and reconstructs using the appropriate algorithm. Thus, system upgrades can maintain a library of older algorithms and/or hardware so as to be able to reconstruct using the proper technique.

In addition it may be desirable to port existing images, generated using systems having different capabilities, to new systems. For example a patient may have compiled a history of mammogram images associated with past screenings. Such a patient may be examined at a facility with updated equipment, for example one that includes a dedicated tomosynthesis system. To compare historical information against existing diagnostic images it may be desirable to store such legacy Mp images, generate Ms images from a tomosynthesis acquisition of the dedicated tomo system and compare like-formatted representations.

Figure 2:
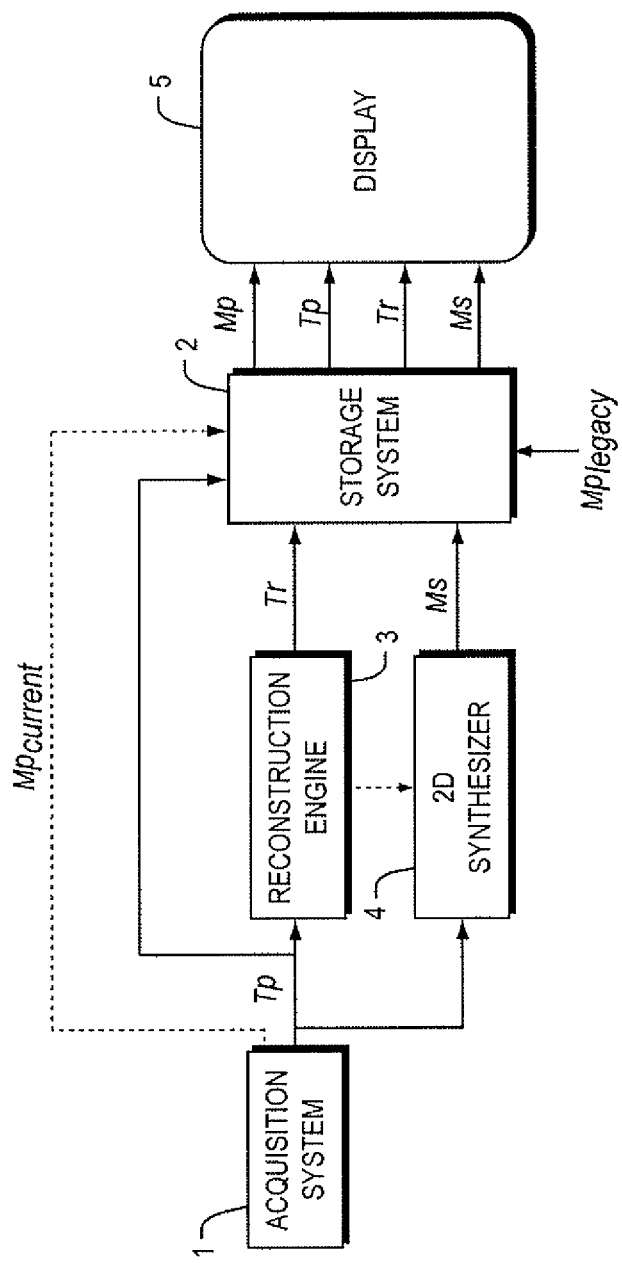
FIG. 2 is a block diagram illustrating flow of data through a system which includes a combination mammography/tomosynthesis acquisition station or a tomosynthesis only acquisition station and where the reconstruction of images Tr occurs before storage of the image data.

Therefore, an alternative design of an image acquisition and display system of the present invention is illustrated in FIG. 2. In this example, the reconstruction unit 3 and 2D synthesizer 4 are directly coupled to the acquisition station 1, and it is the reconstruction images Tr and synthesized images Ms that are sent to storage system 2 for subsequent display on display devices 5, which may also store legacy Mp images. One advantage of the configuration of FIG. 2 is in the way it handles acquisition and synthesizing upgrades—if a new hardware/software version has a modified reconstruction algorithm, then all Tr images and Ms images reconstructed or synthesized from Tp image data taken after the upgrade will automatically reflect this new algorithm, and Tr and Ms images reconstructed or synthesized from Tp image data taken prior to the upgrade will have been reconstructed with the older version and properly stored as such. The images stored on a PACS will be the same as they were viewed by the radiologist or other health professional during the detection/diagnosis or other earlier review. Another advantage of the system of FIG. 2 is the reduced system reconstruction burden compared to the system in FIG. 1, where the reconstruction engine is just prior to the display. If there are multiple acquisition systems, for example four systems that are all pushing images to the display, then the reconstruction engine will need to reconstruct images at 4 times the rate of a reconstruction engine in a system having only one acquisition system, for the same total patient throughput.

Figure 3:
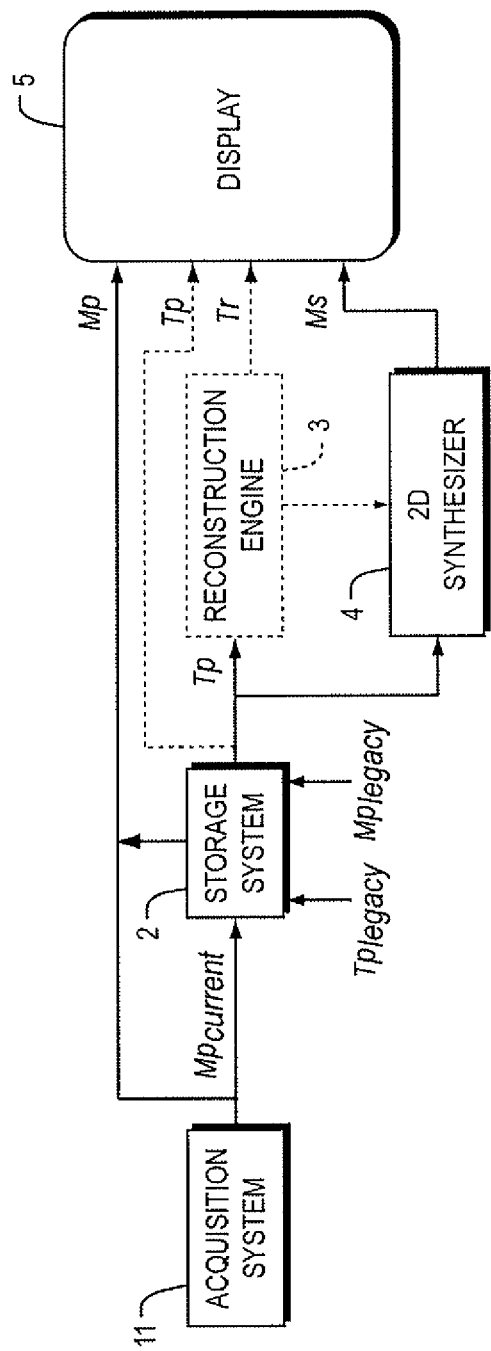
FIG. 3 is a block diagram illustrating flow of data through a system which includes a mammography-only acquisition system, and where reconstruction of tomosynthesis slice images Tr and/or synthesis of the Ms images occurs after storage of acquired tomosynthesis projection images Tp.

FIG. 3 illustrates another image acquisition and display system which may benefit from the 2D image synthesizing process of the present invention. In FIG. 3, the image acquisition device 11 is a mammography only device. One advantage of digital imaging is the portability of data; it is conceivable that patients that switch between different imaging locations may be exposed to imaging equipment with different capabilities. For example, a patient may undergo an exam at an imaging center that includes a tomosynthesis only system, and subsequently undergo an exam at a location that includes a mammography only acquisition system, (or visa versa). In order for the medical professional to easily compare images to identify changes in the breast structure it would be desirable to synthesize a 2D mammogram from existing Tr and/or Tp data. In FIG. 3, storage device 2 is adapted to store both legacy Mp (if any) as well as legacy Tp images. Depending upon capabilities of the display device, (i.e., whether tomosynthesis data can be viewed), the system may include reconstruction unit 3. Other systems which have only the capability of viewing mammograms may not include this unit, and thus the unit and tomosynthesis data are all shown in dashed lines in FIG. 3. In the system of FIG. 3, when a mammogram Mp is acquired, it is either stored in storage device 2 or forwarded to display 5. Tp and/or Tr data are retrieved from the storage device and forwarded to the 2D synthesizer 4. The resulting Ms image is displayed together with the current Mp on display 5. It is envisioned that in such systems the 2D synthesizing software may be provided as a downloadable application that facilitates viewing of tomosynthesis data on existing mammography systems.

The question of which system design will place a greater burden on the PACS storage of an institution will depend upon the sizes of the raw projections Tp and of the reconstructed images Tr. In general, if the raw projections Tp are smaller than the reconstructed images Tr, it might be desirable to save in PACS the raw or preliminarily processed data for Tp images and reconstruct the final Tr images on demand for display or other use. In all cases it may be desirable to keep both of these sizes as small as possible.

One way to reduce the size of an original dataset for a Tp image is to bin the projection Tp data to as large a pixel size as practical without reducing clinical efficacy of the final Ms, Tp or Tr images. Methods that can be used to reduce the Tp image size are described in U.S. patent application Ser. No. 11/271,050, (referred to herein as the '050 application) filed Nov. 10, 2005 by the assignee of the present invention, and incorporated by reference herein.

For storage, transmission to remote locations, and/or other purposes, the images can be formatted consistent with DICOM standards. For example, each raw or displayed projection image set, synthesized image or reconstructed slice image set for a single view is stored as a single Secondary Capture image instance according to DICOM. The image pixel data can be encoded in a selected compressed format (CODEC) that includes all projection or slice images.

As shown in FIGS. 1-3, the imaging and display system of the present invention includes a 2D synthesizer for generating 2D images simulating mammograms taken at both a CC and MLO orientation using a combination of one or more Tp and/or Tr images. A display of the system preferably should be able to display Ms, Mp and Tr (and/or Tp) images concurrently (either in separate windows on the display, on separate monitors of a technology workstation, or overlaid) or sequentially or in toggled mode, wherein the Ms, Mp, Tp and Tr images may be those currently acquired, or those that were acquired in previous studies. Thus, in general, the display can simultaneously or sequentially or in toggled mode display mammograms (Ms, Mp) and tomosynthesis images Tr (and/or Tp) from the current and previous studies. Tr slices can be reconstructed all to the same size, which can be the same as the size of an Mp or Ms image of the breast, or they can be initially reconstructed to sizes determined by the fan shape of the x-ray beam used in the acquisition and later converted to that same size by appropriate interpolate]on/extrapolation.

Images of different types and from different sources can be displayed in desirable size and resolution. For example, an image can be displayed in (1) Fit To View Port mode, in which the size of the displayed image size is maximized such that the entire imaged breast tissue is visible, (2) True Size mode, in which a display pixel on the screen corresponds to a pixel of the image, or (3) Right Size mode, in which the size of a displayed image is adjusted so that it matches that of another image that is concurrently displayed or with which the displayed image is or can be toggled. For example, if two images of the same breast are taken and are not the same size or do not have the same special resolution, provisions are made to selectively zoom in or zoom out one of them, or zoom both, such that they appear to be the same size on the screen when they are concurrently displayed or the user toggles between them, to facilitate comparison or to otherwise facilitate detection/diagnosis. Known interpolation/extrapolation and weighting techniques can be used in such re-sizing, and known image processing technology can be used to make other characteristics of the displayed images similar in a way that facilitates detection/diagnosis.

Figure 4B:
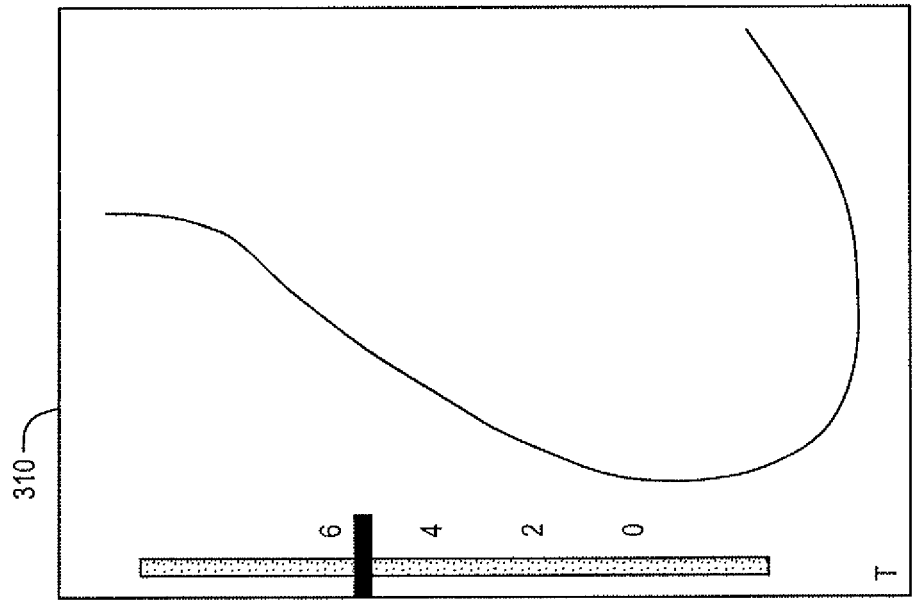
FIGS. 4A-B illustrate a concurrent display of an Ms image and a Tr in substantially same area on a screen, with an example of a non-numeric indication of a thickness and position in the breast of a breast slice represented by a Tr image.
Figure 4A:
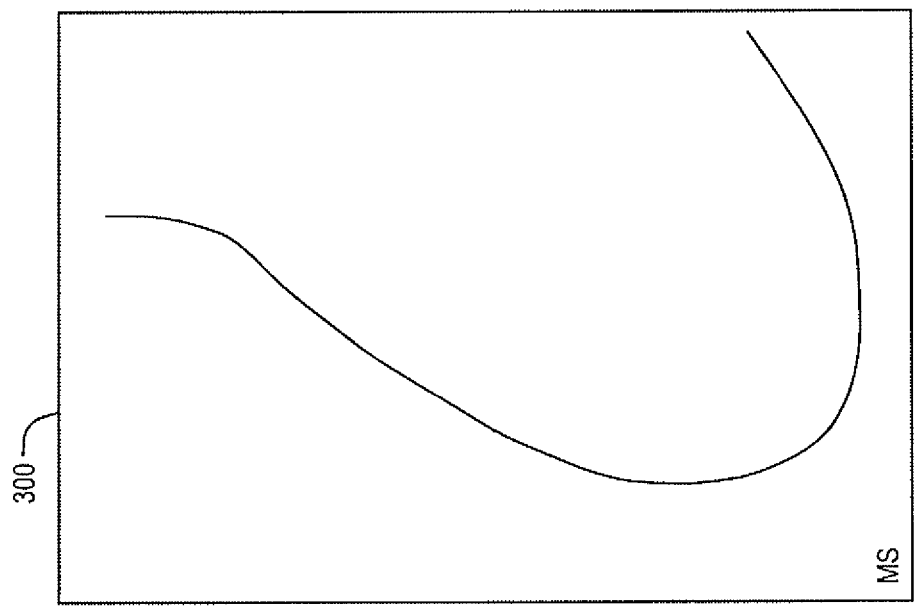

Selected hanging protocols are provided that are unique to the different types of images with which the disclosed system deals. As one example, the hanging protocols for 2D images (e.g. Ms or Mp images) and 3D images (e.g. Tr images) are linked so that when one type of image is displayed for a given breast the other type is displayed as well. For example, when the Ms/Mp image of a breast is displayed, a tile of the Tr images and/or of the Tp images is automatically displayed at the same time, with a desired hanging protocol that may involve scrolling or cine mode presentation, or may require user input so select a particular subset of the Tr and/or Tp images or a particular individual Tr/Tp image. Thus, a combined hanging protocol set can be provided for 2D and 3D images that are concurrently displayed (either on a common display on adjacent displays, or overlaid) or toggled such that only one type is displayed at one time. In addition, the combined hanging protocol can include provisions for linked display of CAD information associated with one or both of the 2D and 3D images involved in the hanging protocol. Alternatively, the hanging protocols for 2D images are made different from those for 3D images. Methods of identifying which image corresponds to which image type in displays of Ms, Mp, Tr and/or Tp images are desirable. One example of such a method is illustrated in FIG. 4. An icon is used to identify an image type. In this non-limiting example, the symbol MS on the left image 300 indicates that it is a synthesized mammogram. The symbol T on the right image 310 indicates that it is a tomosynthesis slice image Tr. Similarly, a symbol Tp (not shown) can be used to indicate that the displayed image is a tomosynthesis projection image Tp, a symbol 2D may be used to indicate that it is a 2D image, and the symbol 3D (also not shown) can be used to indicate that an image on the display is a 3D image. Other symbols/icons serving a similar purpose can be used instead of, or in addition, to those identified above. In the alternative, the images can be displayed without an identification of the type of image. For example, a Tr image and an Mp or Ms image can be displayed at the same time or toggled without displaying an indication of the type of the image that is visible. This may be desirable in cases such as when a user has a familiar hanging protocol and does not need an express identification of the type of image.

Figure 5B:
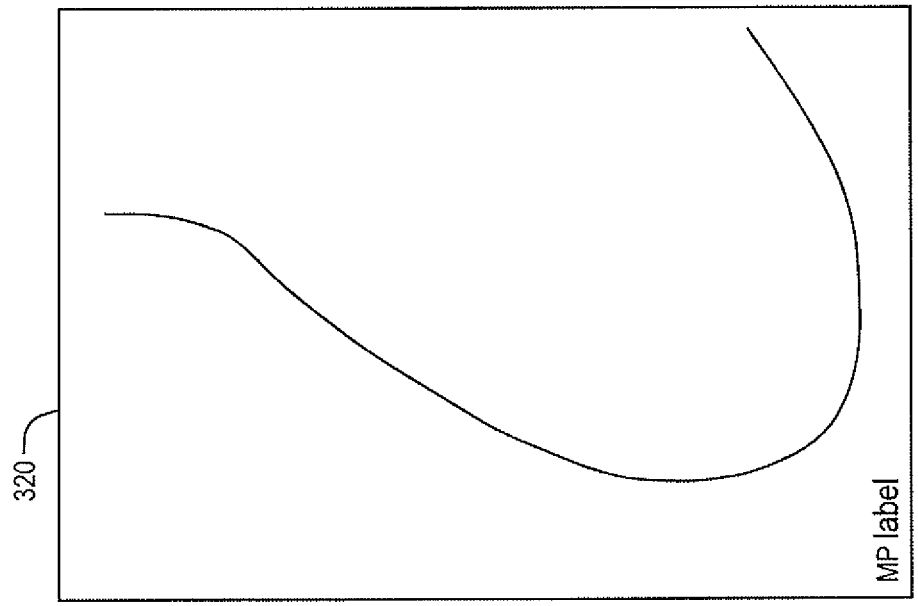
FIGS. 5A-B illustrate a concurrent display of Ms and Mp images, at separate areas on a screen or as combined images.
Figure 5A:
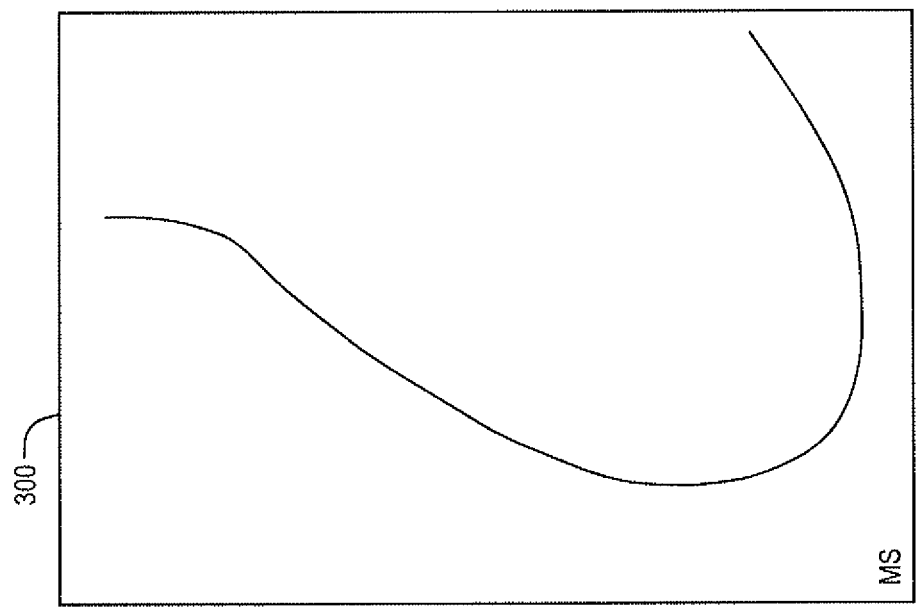

The system described as a non-limiting example in this patent specification is capable of receiving and displaying selectively the tomosynthesis projection images Tp, the tomosynthesis reconstruction images Tr, the synthesized mammogram image Ms and/or the mammogram images Mp, or a single type, or any sub combination of types. It can receive images stored uncompressed, losslessly compressed, and lossyly compressed. It can also include algorithms to decompress images sent in compressed format. The system has software to perform reconstruction of tomosynthesis image data for images Tp into images Tr and software for synthesizing mammogram images Ms. Further, it can include software to generate 3D display images from the tomosynthesis reconstructed images Tr using standard known methods such as MIP (Maximum Intensity Projection), summing, and/or weighted summing algorithms. FIG. 5 illustrates an exemplary display of an Mp image together with a 2D synthesized image; each image may be labeled to indicate whether the image is from a current acquisition, or based on legacy data. For example the Mp image may be a stored legacy mammogram, and the 2D Ms image may be generated from a current tomosynthesis acquisition and may be provided as an initial view to guide the medical professional's perusal of the tomosynthesis data. Alternatively, the Mp image may be based on a current acquisition, for example via a combo mammo/tomo system or by a mammography-only system, and the Ms image may be generated from previously stored tomosynthesis data, such as described in FIG. 3, thereby allowing for comparison of like images to more easily identify regions of interest.

Figure 6B:
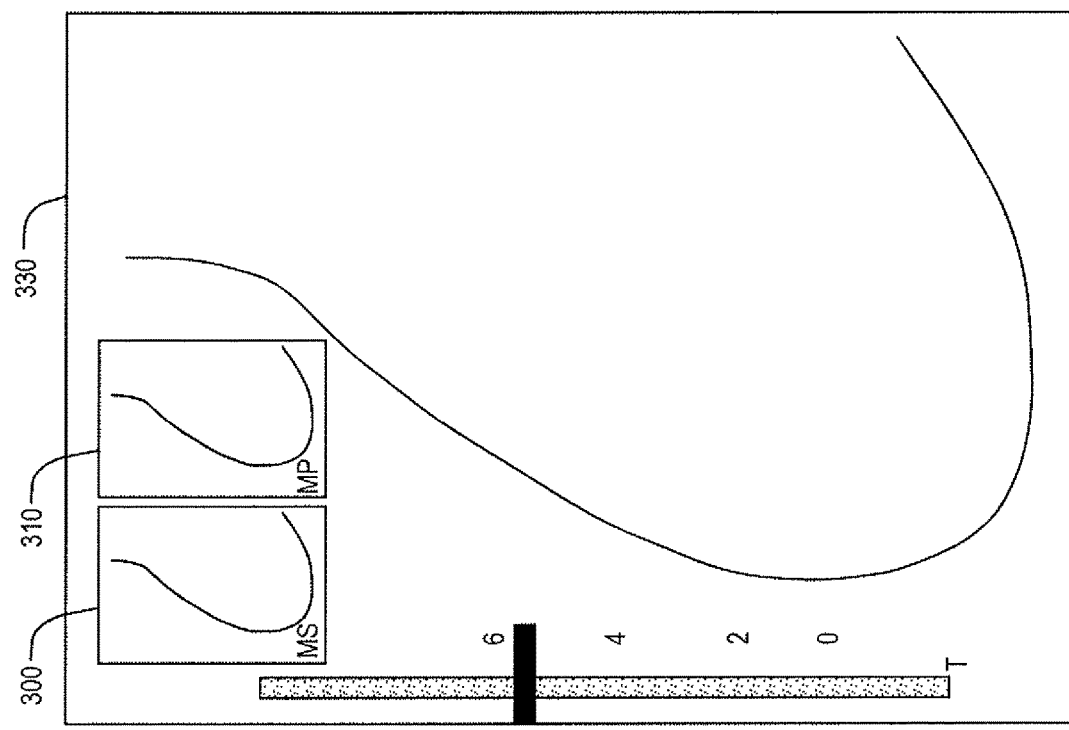
FIG. 6B illustrates a display of a Tr image with an integrated window that includes both an Ms image and a legacy Mp image, shown as scout views, for use in guiding a medical professional's evaluation and workflow using the Tr image data.
Figure 6A:
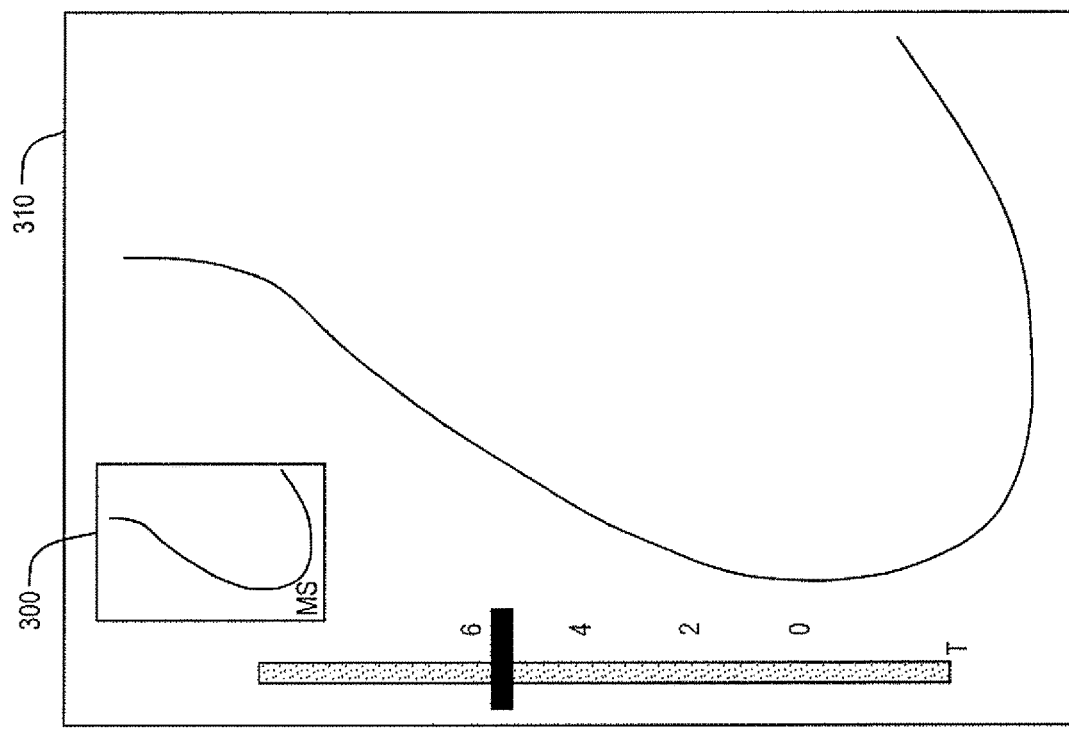
FIG. 6A illustrates a display of a Tr image, with an integrated window including a scout view of a 2D synthesized image, for use in guiding a medical professional's evaluation of the Tr data.

FIG. 6A illustrates the display of the synthesized 2D image as a scout view thumbnail image which may be provided as an overlay in a display of Tp and/or Tr images. Such a scout view may be used to guide the workflow of the medical professional during review of the tomosynthesis images. FIG. 6B illustrates two scout views, showing, for example, a legacy 2D image together with a current 2D image. The ability to compare the two images may further assist the medical workflow. Although FIG. 6B illustrates a legacy Mp image together with an Ms image, any two 2D images associated with differently timed acquisitions could be used, and the present invention is not limited that the particular images shown in the figures.

Figure 7:
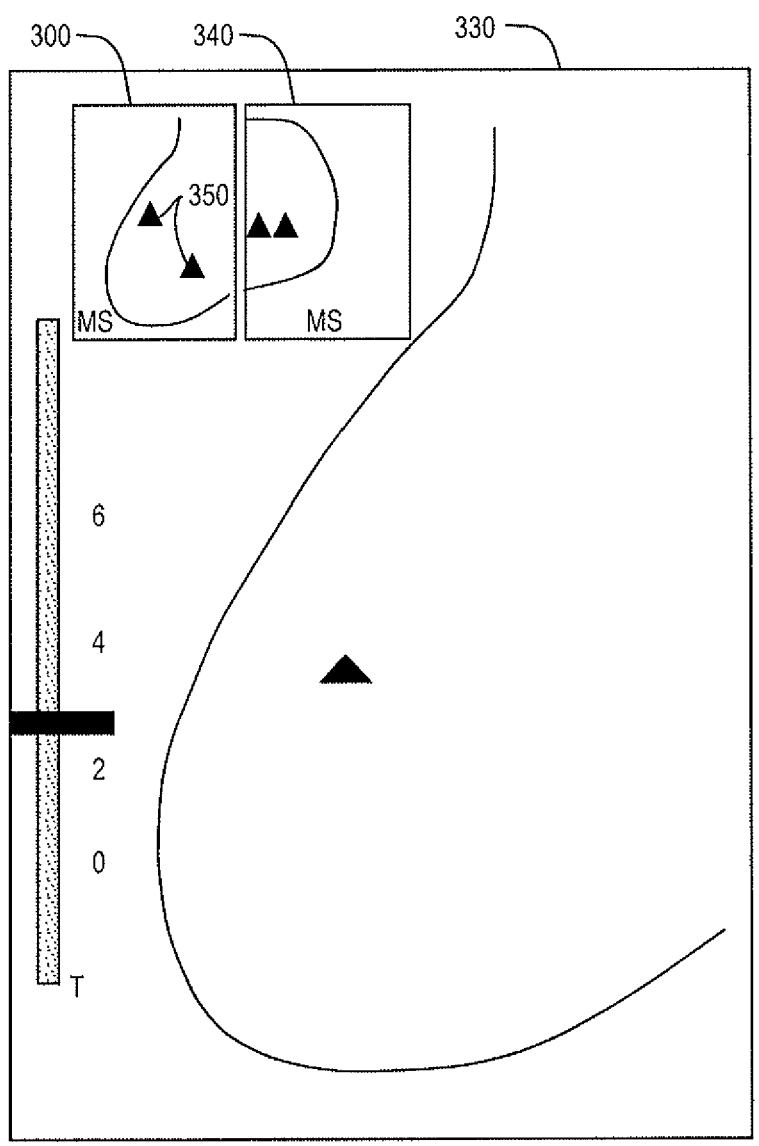
FIG. 7 illustrates a display of Ms/Mp/Tr/Tp images with CAD marks and a non-numeric indication of Tr images in which CAD marks exist.

FIG. 7 illustrates a display of two synthesized 2D images, of different views (CC and MLO). In the embodiment of FIG. 7, a Computer Assisted Detection (CAD) process has been applied to either the synthesized 2D views or alternatively to the reconstructed tomosynthesis data, providing resulting CAD marks 350. As described in the '050 application, the CAD marks resulting from processing a mammogram may be projected onto the 3D tomosynthesis image and visa versa. The present invention further envisions that the CAD marks may be similarly translated across images when using 2D synthesized images.

A variety of methods can be used to select the particular image to be displayed. For example a menu driven interface may be automatically populated with the types of images that are available for display, including both currently acquired images and a selection of available legacy images. Software allows the selection of one or more image planes, for use in image processing, or to change window/level or to change slice height, etc. The menu driven interface may be further populated with display arrangements, including overlaid, cine, inset views, etc. Alternative methods, such as drag and drop techniques can be used to position images on the screen. These sets of images can be on one monitor, or on multiple monitors or other displays.

When more than one image is displayed, it can be convenient to have the images all be displayed at the same pixel spacing, using known interpolation or extrapolation methods applied to digital images. This can facilitate image comparison. As an example, if the prior mammogram was acquired on a system using 100 micron pixel spacing, but the current mammogram was acquired on a system using 70 micron pixel spacing, the display can map the images so the pixel spacings are identical. This pixel spacing adjustment can also be used for Ms, Mp and Tr/Tp images. In a preferred embodiment, (with the exception of thumbnail scout views such as those of FIGS. 6A and 6B) the Ms, Mp and Tr/Tp images are displayed at the same pixel size. This is especially useful in performing overlaid or toggled image display, with the Ms, Mp and Tr/Tp images on top of each other. Thus, an object in a Tr image will appear at the same place as in the corresponding Ms/Mp image. If the two images are not at the same pixel size, toggling between them may show a distracting change due to the difference in pixel size. Matching the pixel spacings for all images on the display is only one possibility. A capability to change the pixel spacings of any image or sets of images, such as would occur when one zoomed a region of a breast, can also be included.

Zooming can be done on any of the images on the display. For example, in a combo overlay display mode, the zoomed area will zoom both the Ms/Mp and the Tr slice images as they are toggled. In other words, no matter what image type is displayed, it will be zoomed. Window/level can be independently, or jointly, applied to any combination of images on the display. In particular, for the Tr images the window/level can be applied to just the single displayed Tr slice image, or all the Tr slice images. If there is a magnified region of an image, window/level can be selectively applied just to the magnified region or to the entire image.

Figure 8B:
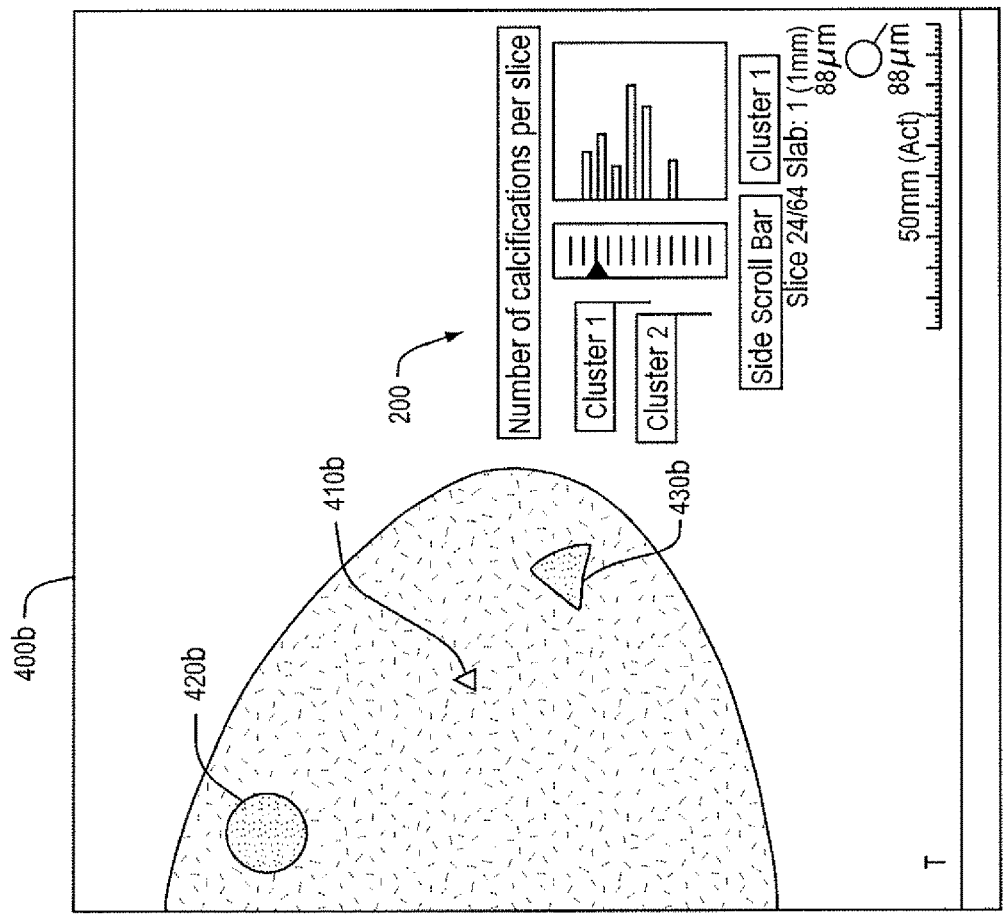
FIGS. 8A-B illustrate a display of an MS image together with a Tr/TP image, wherein a region of interest marker placed in a first image is reflected into a second image.
Figure 8A:
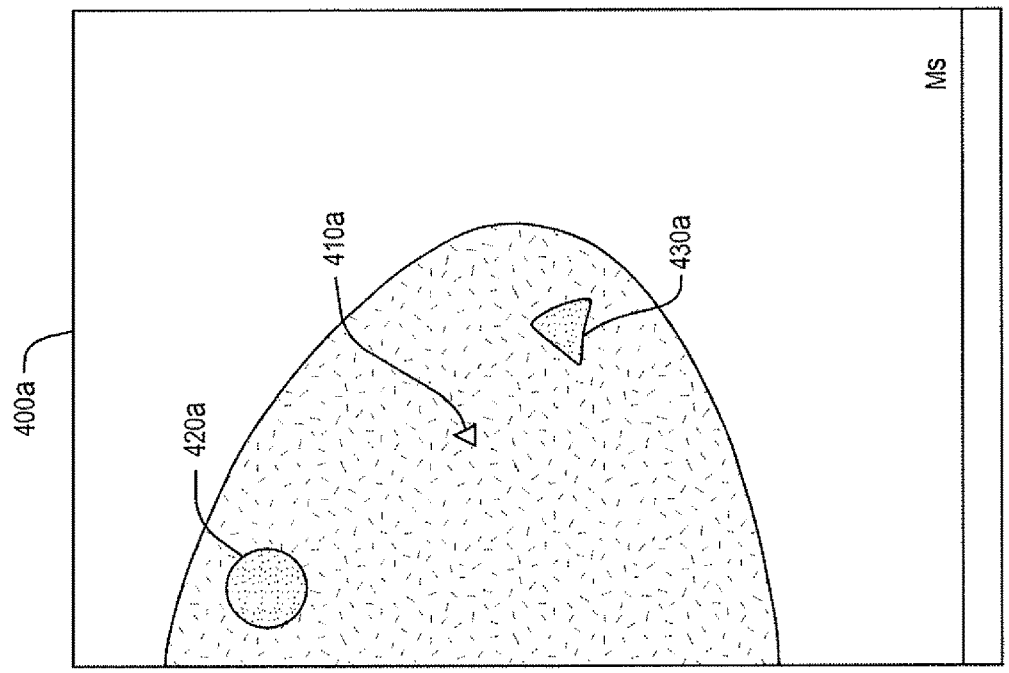

According to another aspect of the invention the synthesized mammogram may be used in conjunction with a tomosynthesis image at the technologist workstation to assist in the identification of tomosynthesis slices associated with regions of interest. For example, referring now to FIG. 8, a technologist or other user may place a marker (410A) or otherwise highlight regions of interest (420A, 430A) on a mammogram. The present invention automatically reflects the marker, by generating a duplicate marker at a corresponding x-y location on the tomographic image 400B as markers 410B, 420B, and 430B. As a user moves the marker do different locations within the image (for example, using a mouse to drag a cursor associated with the mark or region), the reflected mark moves similarly in the alternate image. The automatic reflection of the marker can easily be accomplished using standard graphic imaging techniques because the coordinate systems of the two images have already been aligned for display purposes; thus there will be a one to one relationship between the x-y location of the added mark, and the x-y location on the alternate image where the mark should be reflected. The makers essentially lie on a two-dimensional plane which lies over the respective images, and remain in position as the user scrolls depthwise through the tomographic slice images. Thus the marker will remain over the tomosynthesis slices as the user scroll depth-wise through the tomosynthesis slices. Similarly, the technician may place markers on the tomosynthesis image which are reflected onto the mammogram. With such an arrangement the technician is able to quickly discern how an artifact in the tomosynthesis slice appears in a mammogram image.

Figure 9:
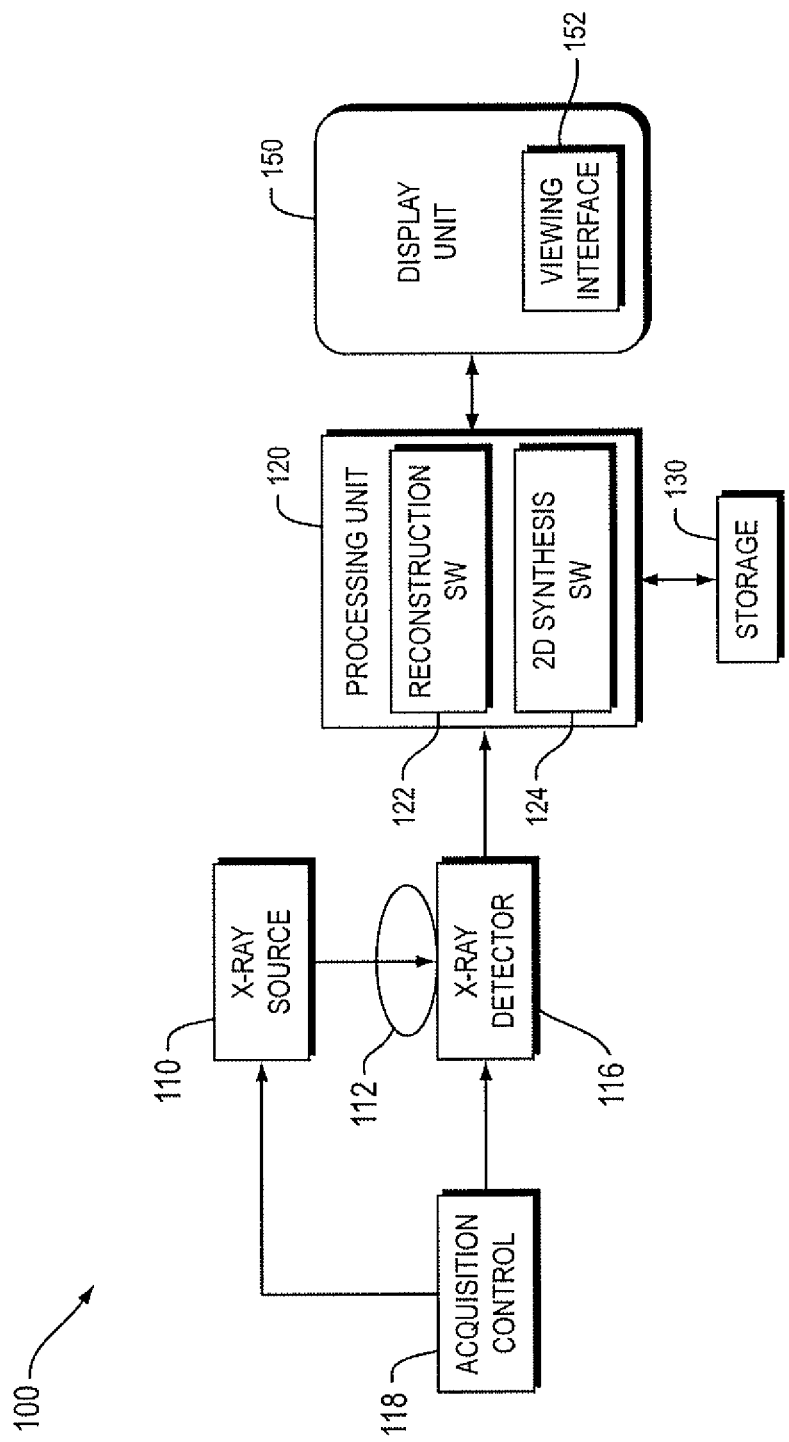
FIG. 9 is a block diagram illustrating exemplary components of an x-ray acquisition and display system that incorporates the 2D synthesis method of the present invention.

FIG. 9 illustrates an overall mammography/tomography system in which the preferred but non-limiting examples discussed above can be implemented. The Figure illustrates in block diagram form an x-ray data acquisition unit 100 that includes an x-ray source 110 imaging a breast 112. An x-ray imager 116 such as a flat panel x-ray imager commercially available from the assignee of this patent specification generates projection image data that can be a mammogram Mp or a tomosynthesis projection image Tp. X-ray source 110 is mounted for movement so that images Tp can be taken at different angles. X-ray imager 116 can be stationary or it can also move, preferably in synchronism with movement of x-ray source 110. Elements 110 and 116 communicate with x-ray data acquisition control 118 that controls operations in a manner known from said earlier-filed patent specifications. X-ray image data from imager 116 is delivered to processing unit 120. Processing unit 120 comprises reconstruction software 122, which may be stored in a computer readable medium of unit 12. The reconstruction software processes x-ray image data as known from said earlier-filed patent application into Tp and Tr image data, which may be stored in storage device 130 and displayed at image display unit 150 as disclosed in the various embodiments described above.

In particular tomosynthesis reconstruction may use any of the methods described in the "Matching Geometry" patent application (Ser. No. 11/667,650) referenced above. The disclosed process and system generate and display tomosynthesis slice images of a patient's breast such that an object in the breast is at same or at least matching relative places in each slice image in which it is visible and, preferably, also at the same or at least matching place as in a conventional mammogram of the same breast. To achieve this, the method and system described in the "Matching Geometry" patent application obtain 2D x-ray projection data for tomosynthesis images preferably using a cone-shaped or pyramid-shaped imaging x-ray beam, and generate tomosynthesis images such that they conform to the same geometric coordinate system as a mammogram and, preferably, to the same coordinate system as a 2D projection mammogram. As a result, anatomical structures appear at geometrically matching or corresponding places in such tomosynthesis images and, preferably, in the mammogram. In one embodiment, the tomosynthesis images can be generated in a two-step computer-implemented process that first reconstructs tomosynthesis images in an initial coordinate system, such as a Cartesian coordinate system, in which objects are not or may not be at matching positions in different tomosynthesis images or in the mammogram, and then projects those images into another coordinate system, such as the coordinate system of the mammogram. In a second embodiment, the reconstruction can directly generate tomosynthesis images in a desired coordinate system, e.g., the cone beam geometry of the mammogram. According to one aspect of the invention, this direct reconstruction can further be projected onto a different coordinate system if desired, for example to modify the plane of reconstruction.

Figure 10:
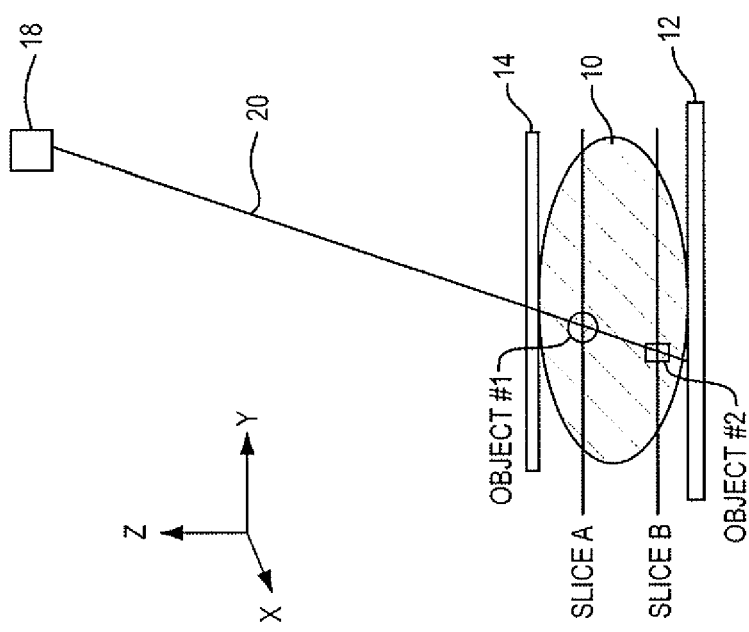
FIG. 10 illustrates image planes of a mammogram and tomosynthesis slice images.

For example, FIG. 10 illustrates a front view where the long axis of the compressed breast 10 is normal to the sheet. The breast 10 is compressed between an image receptor 12, such as a flat panel digital imager, and a compression paddle 14, and is imaged with a cone-shaped or pyramid-shaped x-ray beam 16 from an x-ray source 18. Two objects are illustrated in breast 10, object #1 at slice A and object #2 at slice B. The term object is used here to refer to any structure that can be imaged in a mammogram or a tomosynthesis image, such as a lesion in the breast, and the term slice is used to refer to a layer of the breast of a finite thickness, e.g. thickness in the z-direction, that is less than the total breast thickness. For example, a slice can be a few mm thick, or thinner or thicker. Because the objects #1 and #2 are along the same x-ray trajectory 20, they appear superimposed in a mammogram. However, because x-ray trajectory 20 is not normal to the image plane of receptor 12, as is the general case with x-ray trajectories when using such cone-beam geometry, the two objects appear at different xy locations in tomosynthesis projection images for slice A and slice B. The "Matching Geometries" application describes a reconstruction and display method for tomosynthesis images that matches the coordinates of tomosynthesis images with mammograms. All relevant x-ray measurements can be obtained as respective 2D sets of pixel values (x-ray measurements for elemental picture areas) at each of several different angles of an x-ray beam relative to a breast, e.g. at several equidistant angles over a range. Other raw x-ray data acquisition techniques can be used in the alternative. After pre-processing of the type known in the mammography and breast tomosynthesis art, those pixel values can be reconstructed into a rectangular Cartesian coordinate system (30 in FIG. 11a) using known reconstruction algorithms such as filtered back projection, iterative reconstruction, maximum likelihood reconstruction, or others, for example as taught in said patent application Ser. No. 10/723,486, incorporated herein by reference. As illustrated in FIG. 11a, the voxels (elemental volume elements) that are imaged as respective pixels in the tomosynthesis slice images are aligned along lines normal to the image plane of receptor 12. The result can be conceptualized as a set of pixel values representing x-ray properties of the voxels that are in the 3D space bound by the image plane of receptor 12 at the bottom, compression paddle 14 on top, and on the sides by the boundaries of an x-ray beam 16 that impinges on receptor 12, and are uniformly spaced in xy planes. Because the x-ray beam 16 is cone-shaped, the sides of this 3D space slope at least on three sides of the beam, and the x-ray trajectories from source 18 to receptor 12 diverge in the general case. Thus, in the general case each x-ray trajectory such as trajectory 20 is non-normal to the image plane of receptor 12. Tomosynthesis image slices that match the geometry of the mammogram can be obtained by projecting each of several horizontal breast slices separately onto the image plane of the mammography images, taken along the actual x-ray trajectories included in x-ray beam, using a computer-implemented process adapted without undue experimentation to a particular-xray data acquisition geometry by a programmer of ordinary skill in the art.

Alternatively, for a cone beam x-ray illumination, the reconstruction geometry can be a cone beam coordinate system 31 shown in FIG. 11b, where the voxels that correspond to pixels in the tomosynthesis slice images are at different xy spacings (and differ in size at least in the xy plane) in different slices and corresponding voxels of different slices are along the same (generally sloping) x-ray trajectory. For the reconstruction processing carried out by reconstruction software 122, a geometry matrix can be defined from a geometry calibration file and input projection angles appropriate to the acquisition system 11 for use in backprojection, from fits to the matrix elements determined from a geometry calibration of the acquisition system 11 and input projection angles measured by an encoder in the acquisition system 11. Image processing and filtering can be carried out on the images prior to reconstruction, using image processing techniques known in technologies such as CT scanning and tomosynthesis. A known skin line correction can also be applied at this stage. A backprojection can then be carried out, one tomosynthesis slice at a time, using the geometry matrix as follows:

$$\begin{pmatrix} u \\ v \\ s \end{pmatrix} = (M_i) \begin{pmatrix} x \\ y \\ z \\ 1 \end{pmatrix} \quad \text{Equation I}$$

$$d_x = u/s$$
$$d_y = v/s$$

Where u,v,z is the location of the reconstructed pixel, Mi is the 3×4 geometry matrix for projection I, (x,y,z) is the location of an image pixel, and (dx, dy) is the location on the x-ray detector element or area for the line that connects a focal spot in source 18 and the image pixel.

It is important to note that the geometry matrix (M) is not limited to a Cartesian geometry, or to the acquisition system geometry. Rather the present invention realizes that there may be advantages to reconstructing the data according to the geometry of any coordinate system. FIG. 11c illustrates exemplary virtual cone beam geometry, where the cone beam coordinate system is derived from a hypothetical acquisition system having virtual focal spot positioning. Such a coordinate system, like that of FIG. 11b, has different pixel spacing for each tomosynthesis slice. However, in such an arrangement the angle of pixel spacing close to the chest wall is increased. Other virtual coordinate systems, associated with different hypothetical acquisition system or which focus on different portions of the imaging area may be substituted readily herein within the scope of the present invention.

The above reconstruction methods use a filtered backprojection process to project data to a known geometry. However, other known methods of reconstruction can be used to achieve the same results, including but not limited to iterative reconstruction, maximum likelihood reconstruction, or others, for example as taught in said patent application Ser. No. 10/723,486.

The tomosynthesis image slices to be reconstructed can be parallel to a "default" reference plane as suggested by Equation 1 above. Alternatively, they can be at other desired orientations, defined by a 4×4 matrix multiplication operation applied to the original 3×4 matrix M, according to:

$$\begin{pmatrix} u \\ v \\ s \end{pmatrix} = (M_i) \begin{pmatrix} R_{3\times3} & T_3 \\ O_3^T & I_1 \end{pmatrix} \begin{pmatrix} x' \\ y' \\ z' \\ 1 \end{pmatrix} \text{ where} \quad \text{Equation II}$$

$$\begin{pmatrix} x \\ y \\ z \\ 1 \end{pmatrix} = \begin{pmatrix} R_{3\times3} & T_3 \\ O_3^T & I_1 \end{pmatrix} \begin{pmatrix} x' \\ y' \\ z' \\ 1 \end{pmatrix}$$

For example, a preferred orientation can be an orientation in which a particular mammogram is taken. Alternatively the use of the perspective matrix allows the reconstructed image to be viewed at any orientation. For example, it may be desirable to have several sets of reconstructed data which are related to a common set of projection images, but are reconstructed using different perspectives and coordinate systems.

In summary, reconstructing tomosynthesis slice images can involve: 1.) The selection of the orientation of image slices to be reconstructed. The slice can be either parallel to the "default" reference plane as suggested by Equation I, or at another more preferred orientation, which is defined by a 4×4 matrix multiplication operation to the original 3×4 matrix M, as expressed by Equation II; and 2.) Selection of the reconstruction voxel grid in space, which can be either a Cartesian grid (FIG. 11a) or a Cone beam grid (FIG. 11b) or virtual grid (FIG. 11c).

Processing unit 120 further includes 2D synthesis software which uses one or more of the Tp and/or Tr images to synthesize a 2D image.

There are varieties of methods that can be used to synthesize a 2D image using tomosynthesis data. In a simplest form, any Tp image taken during the tomosynthesis scan may be used as 2D image. Tp images may be used individually, or alternatively a subset of Tp images or a subset of Tr slices (reconstructed using any of the methods above) may be combined, using algebraic methods (averaging, weighted averaging, statistics or other methods), maximum intensity projection, or other known means to provide the 2D image. One example of a method for synthesizing a 2D image will now be described although it should be understood that the present invention is not limited to any particular method of synthesizing a 2D image, but rather encompasses any synthesizing technique which can be used to generate a 2D image from a tomosynthesis data set.

In an exemplary embodiment, a tomo data set consists of Tp0 raw projections, Tp processed projections, and Tr reconstructed slices. The Tp processed projections have been processed as described in the '650 application to perform at least one of coordinate geometry matching and data set size reduction.

A single 'synthesized' 2D image T2d, analogous to the conventional mammography image Mp, is built from the 3D tomo data set alone. As described above, the 2D synthesized image may provide a quick overview of the breast anatomy to facilitate diagnosis and help the radiologist focus on specific regions when analyzing the 3D slices. When reviewing images on the display workstation, the image T2d may replace the Mp image that would normally be present in a combo mode procedure, or may be viewed against legacy Mp images, or displayed in a variety of other combinations.

Figure 12:
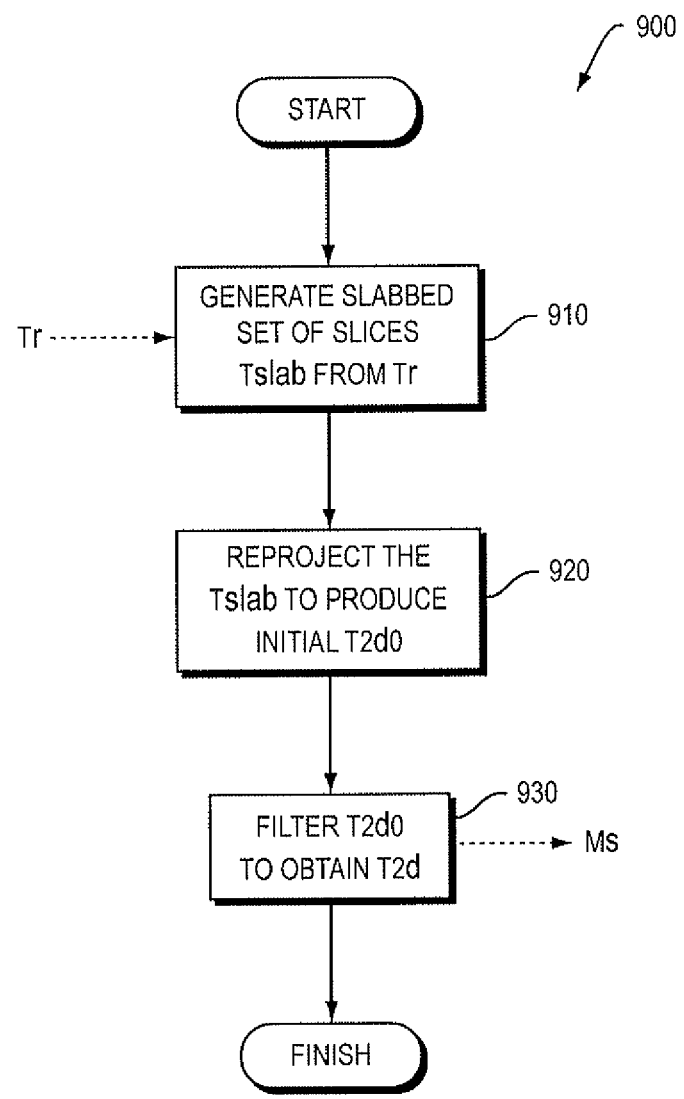
FIG. 12 is a flow diagram provided to illustrate exemplary steps that may be performed in a 2D image synthesis process which uses tomosynthesis data.

FIG. 12 is a flow diagram that illustrates exemplary steps that may be performed in a 2D synthesis process. FIG. 9 assumes that methods described in the '650 application have been used to generate a set of slices Tr as in put to the process, wherein the set of slices are represented in a Cone Beam or Cartesian coordinate system, or alternatively represented in a virtual coordinate system (associated with a virtual acquisition system). It should be understood that although the below equations describe a method using Tr images, similar processing may be performed with any subset of the Tp images.

At step 910, the Tr data set is apportioned into a slabbed set of slices Tslab. That is a number of images Tr are effectively combined, using maximum intensity projection (MIP) or averaging to generate a set of Tslab slices. Equation III below illustrates how the set Tslab is formed using MIP, while Equation IV below illustrates how the set Tslab may be formed using averaging.

Let a slice in the original set be Tr [j, z] where j is the pixel index of the image and z is the slice number.

$$T\text{slab}[j,z] = \text{MAX}(Tr[j, z-N\text{slab}/2], Tr[j, z-N\text{slab}/2+1], \ldots, Tr[j, z+N\text{slab}/2]) \quad \text{Equation III}$$

$$T\text{slab}[j,z] = \text{AVE}(Tr[j, z-N\text{slab}/2], Tr[j, z-N\text{slab}/2+1], \ldots, Tr[j, z+N\text{slab}/2]) \quad \text{Equation IV}$$

At step 920, once the voxel values in the Tslab slices have been selected, the set of slices is re-projected to produce an initial image T2d0. Re-projection methods are well known in the field of image processing. A source point and image plane is chosen, on opposite sides of the image volume. Pixels are obtained by projecting the source point through the slice set to an image plane point. The pixel value is summed at each slice location by interpolating values in the original slices. Note, in the case of cone beam coordinate system reconstruction as described in the '650 application and above, the re-projection is just a sum of pixel values, with no interpolation involved, and is represented by Equation V below:

$$Trep[j, z] = 1/N \sum_{z=z\,min}^{z\,max} Tslab[j, z] \quad \text{Equation V}$$

Where zmin, zmax may be chosen to exclude slices near the breast boundary, or skin. This may reduce artifacts. N=zmax−zmin+1.

Step 930 performs an optional step of filtering the re-projected image to produce T2d. The filtering that is performed should be generally in the direction of the source motion in the original tomosynthesis image acquisition. Although not required, filtering may help reduce additional blur produced in the re-projection due to artifacts in the slices Tr. It is further noted that the filtering step 930 may be performed prior to the re-projection of step 920, but at a computational cost.

The advantages of using the cone beam geometry reconstructed slices as input are as follows. Interpolation at step 920 is simplified because geometric correlation was already performed in the reconstruction. Thus the final image T2d will be registered geometrically with the original set of slices Tr, as described in the '650 application. The registration would facilitate diagnosis as well as the display of CAD results on T2d, where the CAD results are derived from the 3D images Tr. The 3D CAD results may also be re-projected (or summed) as in step 2 and overlaid on T2d.

Accordingly several systems for displaying x-ray images together with 2D images that are synthesized from tomosynthesis image data have been shown and described. The synthesized images may be generated and displayed in conjunction with combination mammography/tomography acquisition stations and tomosynthesis only acquisition stations. The images may even be generated and displayed in combination with mammography only acquisition stations when legacy tomosynthesis data is available. With such an arrangement diagnostic efficiency is increased because the provision of familiar images along with the tomosynthesis data allows historical imaging expertise to be leveraged.

Having described exemplary embodiments, it can be appreciated that the examples described above are only illustrative and that other examples also are encompassed within the scope of the appended claims. It should also be clear that, as noted above, techniques from known image processing and display methods such as post-production of TV images and picture manipulation by software such as Photoshop from Adobe, can be used to implement details of the processes described above. The above specific embodiments are illustrative, and many variations can be introduced on these embodiments without departing from the spirit of the disclosure or from the scope of the appended claims. For example, elements and/or features of different illustrative embodiments may be combined with each other and/or substituted for each other within the scope of this disclosure and appended claims.

The invention claimed is:

1. A system for generating and displaying a synthesized mammogram, the system comprising:
   a computer system, including
      a reconstruction engine configured to receive a tomosynthesis data set, the tomosynthesis data set comprising one or more of a plurality of tomosynthesis projection images and/or one or more of a plurality of tomosynthesis reconstructed slices of a patient's breast, and
      a synthesizer configured to generate a two-dimensional synthesized mammogram from only the tomosynthesis data set, wherein the synthesized mammogram comprises a synthesized two-dimensional image of an entirety of a patient's breast that simulates a conventional mammography image; and
   a display device operatively coupled with the computer system, wherein the computer system is configured to cause the display device to independently or simultaneously display one or more images from the tomosynthesis data set and the synthesized mammogram.

2. The system of claim 1, the computer system further comprising a Computer Aided Detection (CAD) engine configured to analyze the tomosynthesis data set using computer aided detection.

3. The system of claim 2, wherein the computer system is configured to cause the display device to display a CAD mark on the synthesized mammogram.

4. The system of claim 3, wherein the computer system is configured to cause the display device to display the CAD mark on a displayed image of the tomosynthesis data set.

5. The system of claim 4, wherein an x-y location of the CAD mark on the displayed image of the tomosynthesis data set corresponds to an x-y location of the CAD mark on the synthesized mammogram.

6. The system of claim 4, wherein the computer system is configured to cause the display device to display the CAD mark at a same corresponding x-y location on each image of a plurality successively displayed images of the tomosynthesis data set.

7. The system of claim 6, wherein the successively displayed images of the tomosynthesis data set represent differing z-direction depths of the breast.

8. The system of claim 1, wherein the computer system is configured to cause the display device to simultaneously display an image from the tomosynthesis data set and the synthesized mammogram.

9. The system of claim 8, wherein the displayed image from the tomosynthesis data set matches a pixel spacing of the synthesized mammogram.

10. The system of claim 8, wherein the displayed image from the tomosynthesis data set is a tomosynthesis projection image.

11. The system of claim 8, wherein the displayed image from the tomosynthesis data set is a tomosynthesis reconstructed slice.

12. The system of claim 1, wherein the computer system is configured to cause the display device to display indicia indicating a micro-calcification cluster on the synthesized mammogram.

13. The system of claim 12, wherein the computer system is configured to cause the display device to display the indicia on a displayed image of the tomosynthesis data set.

14. The system of claim 13, wherein an x-y location of the indicia on the displayed image of the tomosynthesis data set corresponds to an x-y location of the indicia on the synthesized mammogram.

15. A computer-implemented method for generating and displaying a synthesized mammogram, the method comprising:
receiving a tomosynthesis data set comprising one or more of a plurality of tomosynthesis projection images and/or one or more of a plurality of tomosynthesis reconstructed slices of a patient's breast;
generating a two-dimensional synthesized mammogram from only the tomosynthesis data set, wherein the synthesized mammogram comprises a synthesized two-dimensional image of an entirety of a patient's breast that simulates a conventional mammography image, and
independently or simultaneously displaying one or more images from the tomosynthesis data set and the synthesized mammogram.

16. The method of claim 15, further comprising analyzing the tomosynthesis data set using computer aided detection, and displaying a CAD mark on a respective displayed image of the tomosynthesis data set and on the synthesized mammogram.

17. The method of claim 16, wherein an x-y location of the CAD mark on the displayed image of the tomosynthesis data set corresponds to an x-y location of the CAD mark on the synthesized mammogram.

18. The method of claim 17, further comprising displaying the CAD mark at a same corresponding x-y location on each image of a plurality successively displayed images of the tomosynthesis data set, wherein the successively displayed images of the tomosynthesis data set represent differing z-direction depths of the breast.

19. The method of claim 15, further comprising displaying an indicia indicating a micro-calcification cluster on the on a respective displayed image of the tomosynthesis data set and on the synthesized mammogram.

20. The method of claim 19, wherein an x-y location of the indicia on the displayed image of the tomosynthesis data set corresponds to an x-y location of the indicia on the synthesized mammogram.

* * * * *